United States Patent
Classon et al.

(10) Patent No.: US 6,291,687 B1
(45) Date of Patent: Sep. 18, 2001

(54) ANTIVIRAL PROTEASE INHIBITORS

(75) Inventors: Bjorn Classon, Stockholm; Ingemar Sven-Anders Kvarnstrom, Linkoping; Bengt Bertil Samuelsson, Onsala, all of (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 09/402,499
(22) PCT Filed: Apr. 3, 1998
(86) PCT No.: PCT/SE98/00622
  § 371 Date: Dec. 14, 1999
  § 102(e) Date: Dec. 14, 1999
(87) PCT Pub. No.: WO98/45330
  PCT Pub. Date: Oct. 15, 1998

(30) Foreign Application Priority Data

Apr. 4, 1997 (SE) .................................................. 9701245

(51) Int. Cl.⁷ ................................................ C07D 493/04
(52) U.S. Cl. ........................................ 549/306; 546/284.1
(58) Field of Search ............................................... 549/306

(56) References Cited

U.S. PATENT DOCUMENTS 5,142,056    8/1992    Kempe et al. ...................... 546/265

FOREIGN PATENT DOCUMENTS

0398669 A2    11/1990    (EP) .
0480714 A3    4/1992    (EP) .
WO 94/13629    6/1994    (WO) .

Primary Examiner—Bernard Dentz
(74) Attorney, Agent, or Firm—Birch, Stewart, Kolasch & Birch, L

(57) ABSTRACT

Compounds of the formula I:

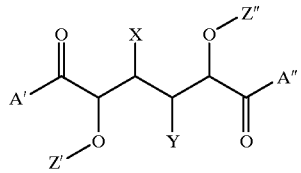

wherein:

A' and A" are independently the same or different group of the formula II:

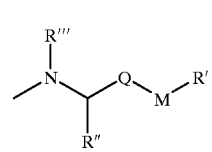

wherein:

R' is H. $CH_3$, $C(CH_3)_2$, —$OR^a$, —$N(R^a)_2$, —$N(R^a)OR^a$ or —DP

R'" is H or $CH_3$; $R^a$ is H, $C_1$–$C_3$ alkyl;

D is a bond, alkylene, —C(=O)—, —S(O)— or —$S(O)_2$—;

P is an optionally substituted, mono or bicyclic carbo- or heterocycle;

R" is H, any of the sidechains found in the natural amino acids, carboxacetamide, or a group $(CH_2)_n$DP;

M is a bond or —C(=O)N(R'")—;

Q is absent, a bond, —CH(OH)— or —$CH_2$—;

or R" together with Q , M and R' define an optionally substituted 5 or 6 membered carbo- or heterocyclic ring which is optionally fused with a further 5 or 6 membered carbo- or heterocyclic ring;

with the proviso that R' is —$OR^a$, —$N(R^a)_2$, —$N(R^a)OR^a$ or —DP, if M is a bond and Q is absent;

X is H, OH, $OCH_3$;

Y is H, OH, $OCH_3$, but X and Y are not both H;

Z' and Z" are independently —$(CH_2)_m$P where P is as defined above;

n and m are independently 0,1 or 2;

and pharmaceutically acceptable salts and prodrugs thereof have utility as aspartyl protease inhibitors of HIV. They can be prepared in a facile two step synthesis from novel 2,5-di-O-benzyl-L-maannaro-1,4:6,3 dilactone intermediates.

13 Claims, No Drawings

ANTIVIRAL PROTEASE INHIBITORS

This application is a 371 of PCT/SE98/00622, filed Apr. 3, 1998.

TECHNICAL FIELD

This invention relates to novel protease inhibitors and in particular to inhibitors of the aspartate protease possessed by certain retroviruses, notably HIV. The invention further relates to the use of such protease inhibitors in the treatment of conditions caused by retroviruses and in the preparation of medicaments for this purpose. The invention also relates to novel synthesis methodology for the facile preparation of protease inhibitors and similar chemical structures.

BACKGROUND OF THE INVENTION

Many biological processes are dependent upon the accurate enzymatic abscission of polypeptides at particular amino acid sequences. An example of such an operation is the post-translational processing of the gag and gag-pol gene products of the human immunodeficiency virus HIV to allow for the organisation of core structural proteins and release of viral enzymes. The enzyme responsible for this task, HIV protease, is a virally encoded homodimeric protease belonging to the aspartic protease family of enzymes. The human renin and pepsin enzymes also belong to this family. Inhibition of the HIV protease in cell culture prevents viral maturation and replication and thus this enzyme represents an attractive target for antiviral therapy against HIV in humans.

There are several references in the patent literature describing inhibitors of HIV protease, typically peptidomimetics having a large number of chiral centres. For example, Abbott Laboratories have extensively investigated linear peptidomimetics as described in a series of patent publication commencing with EP 402 654 and culminating in Abbott's application no. WO 94 14436 describing optimized linear peptidomimetics and in particular the compound Ritonavir:

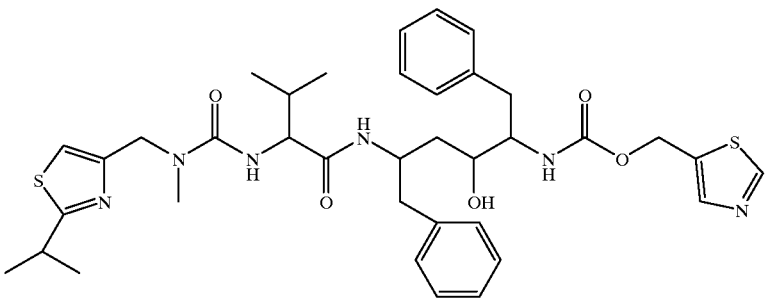

Norvir as this compound is now known, is registered by the FDA and although it has good clinical efficacy, its synthesis is arduous. The synthesis difficulties which have characterized prior art protease inhibitors can be understood by referring to Roche's protease inhibitor saquinavir (Inverase):

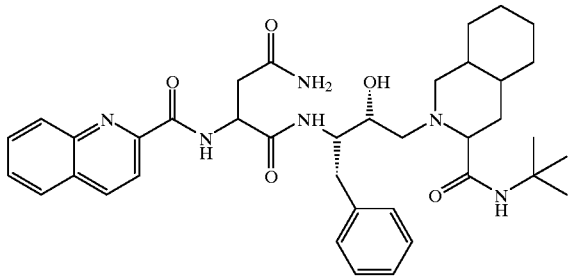

According to literature reports, this compound requires a synthesis route of some 20 steps resulting in an overall yield reputed to be around 2%. This difficult synthetic availability will put pressure on treatment cost and production capacity.

Merck's U.S. Pat. No. 5 413 999 describes indanyl pentamine compounds, including its currently marketed product indinavir:

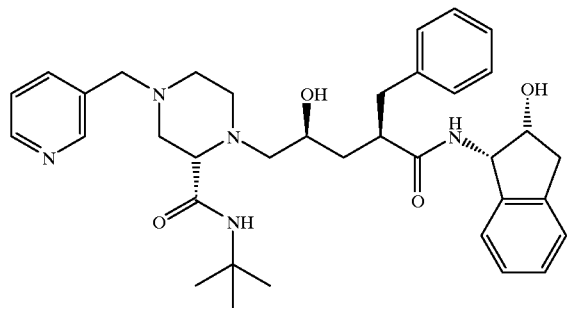

Merck's EP 480 714 discloses a symmetric protease inhibitor having terminal indanolamine groups spaced by a 7 carbon backbone:

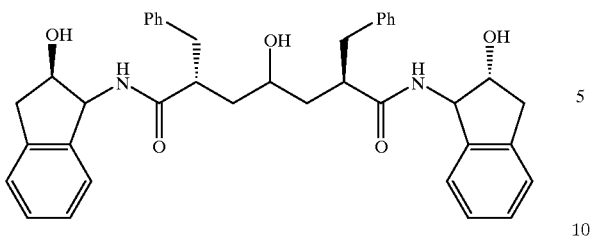

These compounds are prepared by complex methodology starting from an alkenediol.

Banyu's Japanese patent application no 7242613 A also describe symmetric protease inhibitors having indanolamne terminal groups spaced by a 7-carbon backbone:

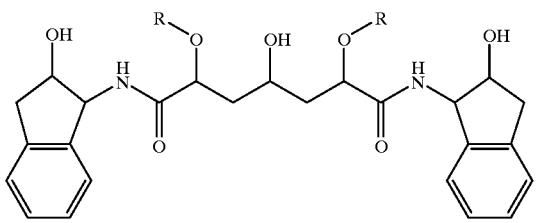

where R is H or lower alkyl. These compounds are prepared by BuLi-alkylation of N,O-isopropylidine-N-[2(R)-hydroxy-(1S)-indanyl]-3-phenylpropanamide with 2-chloro-2-chloromethyl-propene, followed by ozonation, reduction and deprotection.

Vertex' international patent application no WO 94/13629 explores the use of a mannitol carbohydrate precursor to prepare compounds of the formula:

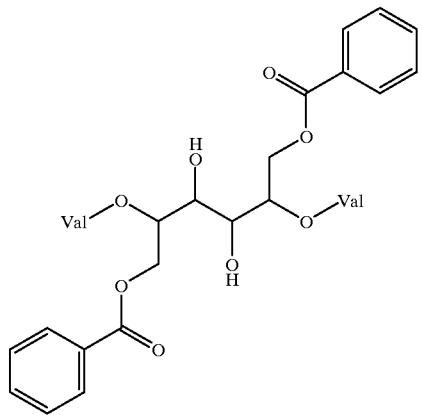

It will be apparent that with these inhibitors, the benzoyl moieties esterified to the C-1 and C-6 hydroxy groups of the mannitol precursor are intended to fill the P1 and P1' pockets of the HIV protease active site. Amino acid functions, such as valyl, are amide bonded to the C-2 and C-5 hydroxy groups and are intended to fill the P-2 and P-2' pockets of the enzyme. These compounds are prepared by bridging the 3-and 4-hydroxy groups with isopropylidine, epoxidising and ring opening the terminal hydroxy groups with a nucleophile such as aryl alcohol followed by amidation of the resulting free hydroxy groups with a respective amino acid. Alternatively the isopropylidine-protected mannitol is first amidated on the more active C-1 and C-6 (terminal) hydroxy groups with the amino acid P-2 filling groups and then esterified with the benzoyl moities on the C-2 and C-5 hydroxy groups.

One of Abbott Laboratories' early patent publications in the protease field, EP 402 646, describes a great number of potential approaches to the construction of protease inhibitors.

One of these approaches also employs a carbohydrate precursor which becomes the central backbone of a symmetric protease inhibitor. Examples 305 and 307 of EP 402 646 describe the ring-opening of a mannosaccharodilactone and the addition of terminal valine esters to form a 3,4-O-isopropylidine-bridged adipamide derivative. The aryl groups which are to fit into the P1 and P1' pockets of the protease are added subsequently via triflate activation at the C-2 and C-5 positions of the carbohydrate backbone and these are later converted to phenylthio groups before the isopropylidine bridge is removed.

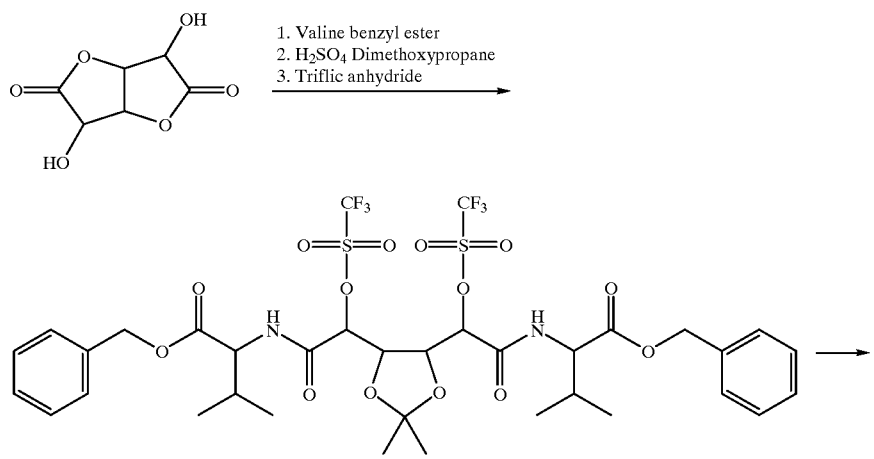

1. Valine benzyl ester
2. H₂SO₄ Dimethoxypropane
3. Triflic anhydride

-continued

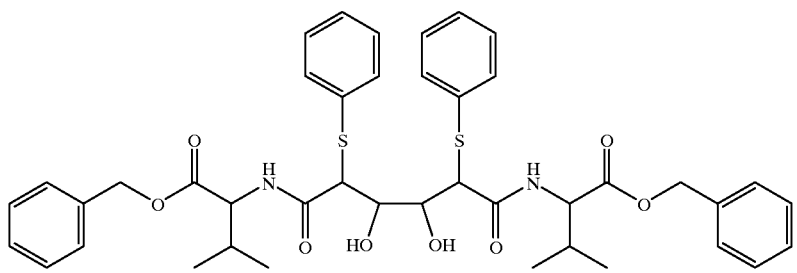

The drawbacks with this process are the inevitable inversion of the configurations of C-3 and C-4 and that while reagents such as thiophenyl can be used to displace the triflate leaving group in the manner shown in EP 402 646, this can only produce thioether derivatives for the P1 and P1' filling groups. At a superficial level it could be thought that the triflate leaving group could be displaced with conventional alkylating reagents such as alkoxide to give an O-alkylated P1/P1' filling group. However we have discovered in this prior art process that the use of alkoxide tends to eliminate the triflates producing an olefin, instead of the desired O-alkylated substituent.

Magnus Björsne et al in "Synthesis of Potential Candidates for Therapeutic Intervention against the Human Immunodeficiency Virus", Stockholm University, 1995 describes the compound

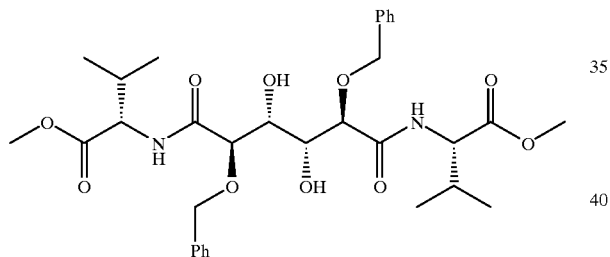

the corresponding benzyl ester and the phenylalanine analog. These compounds are prepared from an L-mannaric acid precursor via the steps of i) bridging the C-3 and C-4 hydroxyls of the hexitol with isopropylidine, ii) protecting the C-1 and C-6 primary hydroxyls, iii) O-alkylating the C-2 and C-5 hydroxyls to the aralkyl ethers, iv) oxidating the C-1 and C-6 primary hydroxyls to carboxylic acids; and v) condensing the resulting compound with the appropriate amino acid (ester) terminal groups This methodology may be graphically represented as follows:

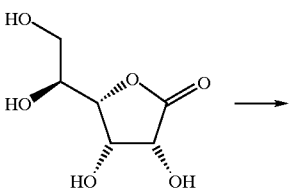

-continued

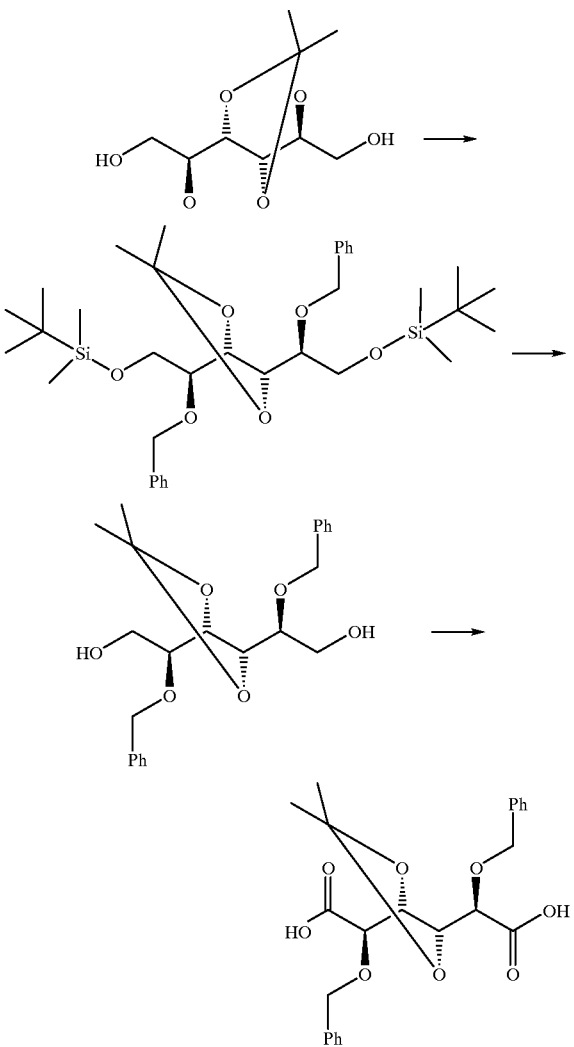

The appropriate valine or phenylalanine (ester) end unit is then condensed onto the terminal carboxyls in dichloromethane-ThF using HOBt-EDC coupling conditions. Despite the need for protection, oxidation and deprotection steps, the Bjorsne synthesis methodology is an improvement over the very large number of steps in conventional peptidomimetic synthesis (see the discussion of saquinavir above). The Bjorsne process also avoids the triflate activation, the preferential reactivity of the "wrong" C-3 and C-4 atoms and other drawbacks of the Abbott EP 402 646 process. However the compounds proposed by Bj örsne have inadequate antiviral properties. The best Bjōrsne compound, where the terminal amines are valine methyl esters (depicted above), has an IC$_{50}$ of 5 $\mu$M which should be compared to currently marketed protease inhibitors which have IC$_{50}$ values one or more orders of magnitude lower.

We have now discovered a novel group of compounds with antiviral properties in the nanomolar IC$_{50}$ range and which lend themselves to a novel carbohydrate based synthesis technique which is even more convenient than those of the prior art discussed above. Accordingly, a first aspect of the invention provides novel compounds of the formula I:

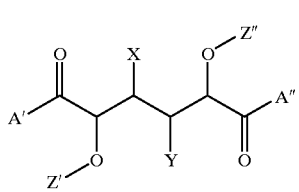

I wherein:
A' and A" are independently a group of the formula II:

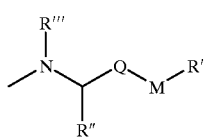

II wherein:
R' is H, CH$_3$, C(CH$_3$)$_2$, —OR$^a$, —N(R$^a$)$_2$, —N(R$^a$)OR$^a$ or —DP
R''' is H, CH$_3$; R$^a$ is H C$_1$–C$_3$ alky;
D is a bond, C$_{1-3}$ alkylene, —C(=O)—, —S(O)— or —S(O)$_2$—;
P is an optionally substituted, mono or bicyclic carbo- or heterocycle;
R" is H, any of the sidechains found in the natural amino acids, carboxacetamide, or a group (CH$_2$)$_n$DP;
M is a bond or —C(=O)N(R''')—;
Q is absent a bond, —CH(OH)— or —CH$_2$—;
or R" together with Q, M and R' define an optionally substituted 5 or 6 membered carbo- or heterocyclic ring which is optionally fused with a further 5 or 6 membered carbo- or heterocyclic ring;
with the proviso that R' is —OR$^a$, —N(CH$_3$)$_2$, —N(R$^a$)OR$^a$ or —DP if M is a bond and Q is absent;
X is H, OH, OCH$_3$;
Y is H, OH, OCH$_3$, but X and Y are not both H;
Z' and Z" are independently —(CH$_2$)$_m$P where P is as defined above;
n and m are independently 0,1 or 2;
and pharmaceutically acceptable salts and prodrugs thereof. Compounds of the formula I are active inhibitors of aspartyl proteases, such as those from HIV. Further aspects of the invention thus provide:
   a pharmaceutical formulation comprising a compound of the formula I in admixture with a pharmaceutical acceptable carrier or diluent;
   the use of a compound of the formula I in the manufacture of a medicament for the prophylaxis or treatment of conditions, such as AIDS caused by retroviruses, such as HIV; and
   a method for treating conditions caused by retroviruses, especially AIDS in humans, comprising administering a compound of formula I to a subject afflicted with said condition.

The compounds have a relatively low molecular weight and should therefore provide good oral absorption properties in mammals. In contrast to prior art aspartyl protease inhibitors, the compounds of the invention can be conveniently prepared with a small number of steps from readily available and cheap starting materials, such as L-mannarodilactone or its commercially available precursors or derivatives, such as L-mannonic-γ-lactone.

A further aspect of the invention thus provides a method for the preparation of a compound of the formula I

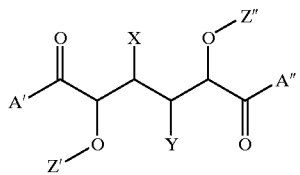

where X, Y, Z' and Z" are as defined above and each of A' and A" are independently:
   a group of the formula II or a conventional protease P-2/P-2' filling group, the method comprising
      i) O-alkylation of an L-mannaric-1,4:6,3-di-lactone to form the Z' and Z" groups,
      ii) opening of the lactone with similar or different primary or secondary amines to form the respective A' and A" groups; and
      iii) optional conversion of the C-3 and C-4 to the appropriate X and Y" groups.

An example of this method aspect of the invention can be depicted as follows:

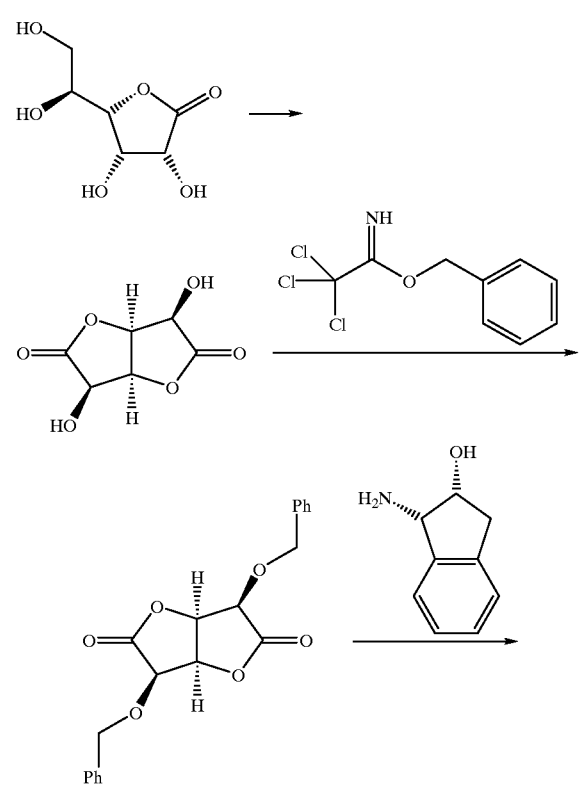

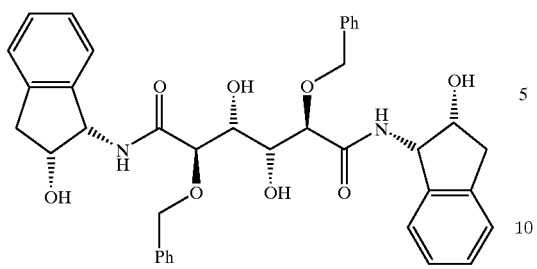

The method aspect of the invention is preferably used to produce the compounds of formula I as claimed herein, but can also be used to prepare protease inhibitors with conventional protease P-2/P-2' filling groups.

Introduction of the Z' and Z" groups as ethers of the C-2 and C-5 hydroxyls in step i) is conveniently carried out by O-alkylation with the appropriate derivative: $E(CH_2)_nP$ where E is a halogen, mesylate, tosylate etc and P and n are as described above in the presence of a base such as a carbonate, metal hydride or hydroxide and an aprotic solvent such as N,N-dimethylfonnamide, tetrahydrofuian or acetone. Conveniently the alkylating agent is benzyl trichloroacetimidate in conjunction with a proton or a Lewis acid, e.i. trimethylsilytriflate.

The ring opening in step ii) to introduce the amino or amino acid derivatives A' and A" are carried out using standard conditions in solvents such as dioxane, nitromethane THE, diglym, DMF or DMSO, which are preferably chosen to dissolve both the carbohydrate derivative and the particular amine involved.

For ease of synthesis it is generally preferred that the terminal arnines A' and A" are identical. However, although the target enzyme is a symmetric dimer, thus implying a tight interaction with symmetric compounds, it can in some circumstances be advantageous for resistance or pharmacokinetic reasons etc to have asymmetric terminal amines. Where is it is desired to have an asymmetric compound, that is where the A' and A" groups differ, it will generally be most convenient to add the respective A' and A" groups sequentially. This can be done in conjunction with appropriate protection of one of the rings of the dilactone, but may also be achieved by manipulation of the reagent concentrations, reaction conditions, speed of addition etc to provide a monoaminated lactone which is separated by conventional techniques or amine neutralization, prior to reaction with the second A' or A" amine.

Alternatively the differential terminal amination can be achieved with a solid phase synthesis where the unaminated or partially aminated lactone is secured to a solid phase substrate, such as polymer beads of which many are known in solid phase chemistry, for instance Merrifield resin. Immobilization of the lactone in this fashion will only allow amination on a defined lactone ring Scheme 1 below outlines such a scheme in the context of combinatorial synthesis of a library of compounds in accordance with the invention, but it will be apparent that single pure compounds can be prepared by similar methodology, but using pure reagents.

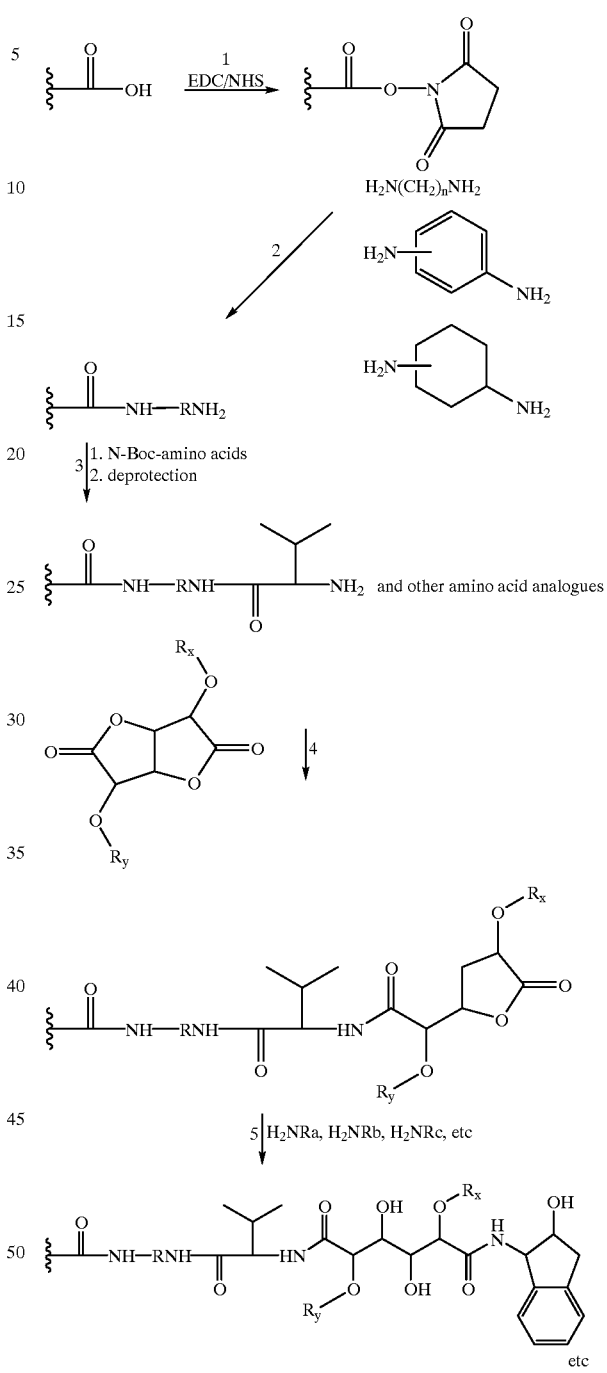

SCHEME 1

In Scheme 1, steps 1 and 2 comprise the preparation of a linking group on the carboxy groups of the resin beads. Linkers of various lengths, rigidities and differential cleavabilities (several are listed against step 2) can be used as is conventional in the solid phase chemistry art. In step 3, the free amine on the linker-equipped solid phase bead is amide bonded with an N-protected amino acid under standard peptide chemistry conditions. The amino acid reagent comprises a number of different, protected amino acids, such as N-Boc valine, N-Boc isoleucine, N-Boc alanine, N-Boc lencine etc and thus this reaction step results in a first combinatorial chemistry tier. The solid phase beads now bear a plurality of randomly disposed amino acids each spaced by a respective linker from the carboxy surface of the bead.

In step 4 the free amine (after deprotection of the N-Boc groups) on the amino acid array is used to ring-open a di-O-alkylated γ-dilactone, wherein $R_x$ and $R_y$ are the same or different optionally substituted (hetero)arylalkyl groups, for instance benzyl, fluorobenzyl, pyridylmethyl etc. This ring opening is carried out under conventional conditions, as exemplified below, in solvents such as dioxane, nitromethane, THF, diglym, DM, DMSO and the like. If $R_x$ and $R_y$ are different (hetero)arylalkyl groups, this step will thus produce a farther tier of combinatorial variation, depending on whether the $R_x$- or $R_y$-bearing ring is opened. However, the dilactone reagent itself may comprise a plurality of different dilactones with various combinations of $R_x$, $R_y$ and/or stereochemistry of the lactone, leading to an even greater spread of combinatorial diversity.

In the fifth step, the remaining ring of the now-immobilized lactone is ring opened in a corresponding fashion with a further amine reagent. Once again this amine reagent may comprise a mixture of different amines, for instance L-amino acids or (hetero)cyclic amines such as the one depicted. Thus this step too may create a further tier of combinatorial diversity. The combinatorial library is cleaved from the linker using its appropriate cleavage reagent, typically a specific anidase or change in pH etc.

Although the compounds of formula I are preferably prepared by the method aspect of the invention, it is also possible to employ the initial steps of the Björsne technique described above in conjunction with the appropriate choice of A' and A" amines, followed where necessary by post-modification of X and Y as discussed above and exemplified in the following Example 2.

Preparation of compounds of Formula I in which X is hydrogen can be conveniently done by deoxygenation as illustrated in the accompanying Examples 2 and 26. The preferred stereochemistry is the 2R, 3R, 4R, 5R form.

Carbocyclic groups for R' as —DP and/or Z'/Z" and/or the optional substituents thereto may be saturated, unsaturated or aromatic and include monocyclic rings such as phenyl, cyclohexenyt, cyclopentenyl, cyclohexanyl, cyclopentanyl, or bicyclic rings such as indanyl, napthyl and the like Heterocyclic groups for R' as —DP and/or Z'/Z" and/or the optional substituents thereto may be saturated, unsaturated or aromatic and have 1 to 4 hetero atoms including monocyclic rings such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyimidinyl, pyridazinyl, oxazolyl, oxazolidinyl, isoxazolyl, isoxazolidinyl, morpholinyl, thiazolyl, thiazolidinyl, isothiazolyl, isothiazolidinyl, and the like or bicyclic rings especially of the above fused to a phenyl ring such as indolyl, quinolinyl, isoquinolinyl, benzimidazolyl, benzothiazolyl, benzoxazolyl, benzothienyl etc. The carbo or heterocyclic ring may be bonded via a carbon or via a hetero atom, typically a nitrogen atom, such as N-piperidyl, N-morpholinyl etc.

Preferred embodiments of Formula II for the A'/A" groups of the compounds of the invention include those of the formula IIa or IIe:

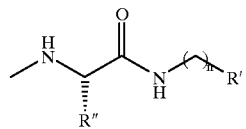

IIa where n is 1 or 2 and R' is alkyloxy, preferably metbyloxy, or those where n is 0 and R' is methyl.

Other preferred groups of fonnula II include IIb below

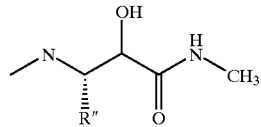

IIb

An alternative preferred configuration for the A'/A" groups of the compounds of the invention includes groups of the formula IIc:

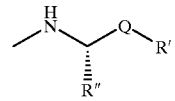

IIc where Q is a bond, methylene or —C(OH)— and R' is —OR$^a$, —N(R$^a$)$_2$, —NR$^a$ OR$^a$, where R$^a$ is H or C$_1$–C$_3$ alkyl, or a carbo- or heterocyclic group including N-piperidine, N-morpholine, N-piperazine, pytrolyl, irnidazolyl, pyrazolyl, pyridyl, pyrimidyl, pyrazinyl etc.

A favoured subset of compounds within formula IIc has the formula IId:

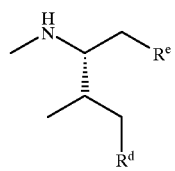

IId where R$^d$ is hydrogen or methyl (that is a valyl or isoleucyl side chain) and R$^c$ is

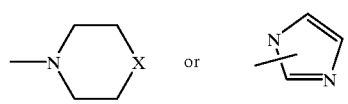

where X is methylene, O, S, S=O, S(=O)$_2$ or NH or R$^c$ is —N(CH$_3$)$_2$, —NHOH, —NHOMe, —NHOEt, —NMeOH, —NMeOMe etc.

In each of formulae IIa, IIb and IIc, R" is hydrogen, methyl, ethyl, isopropyl, cycloalkyl such as cyclopropyl, cyclobutyl or cyclohexyl, cycloalkenyl benzyl, carboxacetamide or 4-imidazolylmethy, any of which may be substituted as defined above. Preferred R" groups include the side chains found in the natural amino acids, especially those of leucine, asparagine, histidine or proline. The most preferred R" groups for formula IIa, IIb, IIc and IId are the isoleucyl and especially the valyl side chain.

R' will vary depending on the nature of Q and/or M, if present, and may for instance be selected from hydrogen, methyl, ethyl, isopropyl, $R^e$ as defined above, valinol, a heterocycle such as pyridyl, thiazole, oxazole, imidazole, N-piperidine, N-morpholine, N-piperazine, pyrrolyl, imidazolyl, pyrazolyl, pyrimidyl, pyrzinyl, any of which R' groups may be substituted as defined for Z'/Z" below.

Further favoured A'/A" groups include those of formula II where R", Q, M and R' together define an optionally substituted 5 or 6 membered carbo- or heterocylic ring. A preferred group within this definition include groups within formula III:

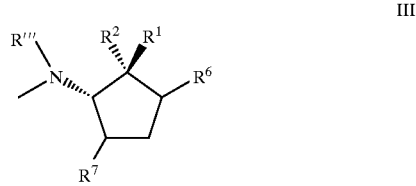

III where
R''' is as defined above,
R¹ is H, $NR^4R^4$, C(=O)$R^3$, $CR^3R^4$ or a monocyclic, optionally substituted carbo- or heterocycle;
R² is OH, or together with R¹ is =O, or if R¹ is $NR^4R^4$, then R² may be H;
R³ is H, halo, $C_1$–$C_3$ alkyl, $OR^5$, $NR^4R^4$;
R⁴ is H, $C_1$–$C_3$ alkyl;
R⁵ is H or a pharmaceutically acceptable ester;
R⁶ is OH, $NH_2$, carbamoyl or carboxy;
R⁷ is hydrogen, $C_1$–$C_4$ straight or branched alkyl or together with the adjacent carbon atoms forms a fused phenyl or heteroaromatic ring;

Preferred groups of formula III include aminoindanol and 1-amino-azaindan-2-ol, that is moieties of the formulae:

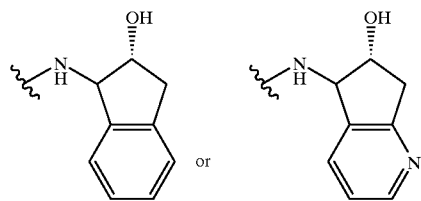

Conventional protease P-2/P-2' filling groups for A'/A" include those found in Roche's saquinavir and Abbott's ritonavir compounds. Additional examples of conventional P-2/P-2' filling groups include those found in Vertex' VX 478, Agouron's AG1343 (now known as nelfinavir) and Merck's indinavir, as depicted above.

Optional substitutents for the carbo- or heterocyclic moiety of Z'/Z" or A'/A" include one to three substituents such as halo, amino, mercapto, oxo, nitro, $NHC_1$–$C_6$ alkyl, $N(C_1$–$C_6$ alkyl$)_2$, $C_1$–$C_6$ alkyl, $C_1$–$C_6$ alkenyl, $C_1$–$C_6$ alkynyl, $C_1$–$C_6$ alkanoyl, $C_1$–$C_6$ alkoxy, thio$C_1$–$C_6$ alkyl, thio$C_1$–$C_6$ alkoxy, hydroxy, hydroxy$C_1$–$C_6$ alkyl, halo$C_1C_6$ alkyl, amnino$C_1$–$C_6$ alkyl, $C_1$–$C_6$ alkyl, cyano, carboxyl, carbalkoxy, carboxamide, carbamoyl, sulfonylamide, benzyloxy, nmorpholyl-$C_1$–$C_6$ alkyloxy, a monocyclic carbo- or heterocycle, as defined above, a carbo- or heterocyclic group spaced by alkyl, such as $C_{1-3}$ alkylaryl, etc.

The preferred definitions for Z' and Z" include benzyl, unsubstituted or substituted with 1, 2 or 3 substituents, especially 1 selected from fluoro, chloro, hydroxy, amino, —NH($C_{1-6}$ alkyl), —N($C_{1-6}$ alkyl)$_2$, —NPh($C_{1-6}$ alkyl), —NHPh, methoxy, cyano, hydroxymethyl, arninomethyl, alkylsulfonyl, carbamoyl, morpholinethoxy, benzyloxy, benzylamide etc. Other possibilities exhibiting the great freedom in this area are shown in the examples. It will be apparent that the substituent to Z' and/or Z" may comprise a ring structure (which substituent ring structure is itself substituted as defined herein) such as phenyl or a 5 or 6 membered heterocycle containing one or two betero atoms such as thiophene, pyridine etc. The preparation of useful heterocyclic substituents for Z' and Z" as benzyl are described in Tetrahedron Letters 1997 6359-6359-6367 and J Org Chem 62 (1997) 1264 and 6066, including N-morpholine, N-piperidine, N-piperazine, N'-methyl-N-piperazine, N-pyrrolidone, N-pyrrolidine and the like.

Such substituents may be in the meta but especially the ortho or para positions of Z'/Z", with small groups such as fluoro being favoured for the ortho and meta and with extensive freedom for larger groups in the para such as (optionally substituted) cyclic substituents, including the N-bonded rings in the immediately preceding paragraph. The whole Z' and Z" group or their respective carbo-or heterocyclic moiety may be different but for ease of synthesis it is convenient if they are the same.

Appropriate pharmaceutically acceptable salts, both for A'/A" as a free acid or for other charged groups along the compound of formula I include salts of organic carboxylic acids such as acetic, lactic, gluconic, citric, tartaric, maleic, malic, pantothenic, isethionic, oxalic, lactobionic, and succicic acids, organic sulfonic acids such as methanesulfonic acid, ethanesulfonic acid, benzenesulfonic acid, p-chlorobenzenesulfonic acid and p-toluenesulfonic acid; and inorganic acids such as hydrochloric, hydroiodic, sulfuric, phosphoric and sulfanic acids.

Prodrugs of the invention are derivatives that release a compound of formula I in vivo, generally by hydrolysis or other metabolic interaction in the intestine, liver or plasma. Typical prodnigs are esters formed on free hydroxy groups in the compounds. Appropriate pharmaceutically acceptable esters include $C_1$–$C_{22}$ fatty acid esters, where the fatty acid is unsaturated, monounsaturated or multiply unsaturated. Saturated fatty acid esters include short chains such as acetyl or butyryl or long chain such as stearoyl. Unsaturated fatty acid esters are preferably in the ω-9 series, such as palmitoleic or linolenic esters. Other esters include $C_1$–$C_6$ alkylaryl esters such as benzyl or methylpyridyl or esters of phosphoric acid, such as monophosphate. Alternative esters include the corresponding fatty acid or alkylaryl carbonate, carbamate or sulphonic esters.

Presently favoured compounds of Formula I include
N1,N6-di[(1S)-2-methyl-1-(methylcarbamoyl)propyl]-(2R,3R, 4R,5R)-2,5-di(benzyloxy)-3,4-dihydroxyhexanediamide,
N1,N6-di[(1S)-2-methyl-1-(methylcarbamoyl)propyl]-(2R, 3S,5R)-2,5-di(benzyloxy)-3-hydroxyhexanediamide,
N1,N6-di[(1S)-2-methyl-1-(methyl carbamoyl)propyl]-(2R,3R,5R)-2,5-di(benzyloxy)-3-hydroxyhexanediasnide,
N1,N6-di[(1S)-2-metbyl-1-(methylcarbainoyl)butyl]-(2R,3R,4R,5R)-2,5-diabenzyloxy)-3,4-dihydroxyhexanediamide,
N1,N6-di[(1S)-1-(methylcarbamoyl)-2-phenylethyl]-(2R,3R,4R,5R)-2,5-di(benzyloxy)-3,4-dihydroxyhexanediamide, N1,N6-di[(1S)-1-(metbylcaramoyl)-2-(4-hydroxyphenyl)ethyl]-(2R,3R,4R,5R)-2,5-di(benzyloxy)-3,4-dihydroxyhexanediamide, N1,N6-di[(1S)-2-methyl-1-(methylcarbamoyl)propyl]-(2R,3R,4R,5R)-2,5-di[(4-fluorobenzyl)oxy]-3,4-dihydroxyhexanediarnide, N1,N6-di[(1S)-2-methyl-1-(cyclopropylcarbamoyl)propyl]-(2R,3R,4R,5R)-2,5-di(benzyloxy)-3,4-dihydroxyhexanediamide, N1,N6-di[(1S)-2-methyl-1-(methylcarbamoyl)propyl]-(2R,3R,4R,5R)-2,5-di[(2-methylbenzyl)oxy]-3,4-dihydroxyhexanediamide, N1,N6-di[(1S,2R)-2-hydroxy-2,3-dihydro-1H-1-indenyl]-(2R,3R,4R,5R)-2,5-di(benzyloxy)-3,4-dihydroxyhexanediamide, N1-[(1S,2R)-2-hydroxy-2,3-dihydro-1H-1-indenyl]-N6-[(1S)-2-methyl-1-(methylcarbamoyl)propyl]-(2R,3R,4R,5R,)-2,5-di(benzyloxy)-3,4-dihydroxyhexanedianide, N1,N6-di[(1S,2R)-2-hydroxy-2,3-dihydro-1H-1-indenyl]-(2R,3R,4R,5R)-2,5-di(2-fluorobenzyloxy)-3,4-dihydroxyhexanediamide, N1,N6 -di[(1S,2R)-2-hydroxy-2,3-dihydro-1H-1-indenyl]-(2R,3R,4R,5R)-2,5-di(4-fluorobenzyloxy)-3,4-dihydroxyhexanediamide, N1,N6-di[(1S,2R)-2-hydroxy-2,3-dihydro-1H-1-indenyl]-(2R,3R,4R,5R)-2-(benzyloxy)-5-(4-methylbenzyloxy)-3,4-dihydroxyhexanediamide, N1,N6-di[(1S)-2-methyl-1-(methylcarbamoyl)propyl]-(2R,3R,4R,5R)-2,5-di[(4-phenylbenzyl)oxy]-3,4-dihydroxyhexanediamde, N1,N6-di[(1S)-2-methyl-1-(metbylcarbamoyl)propyl]-(2R,3R,4R,5R)-2,5-di[4-(3-thienyl)benzyloxy]-3,4-dihydroxyhexanediamide, N1,N6-di[(1S)-1-phenyl-1-(methylcarbamoyl)methyl]-(2R,3R,4R,5R)-2,5-di(benzyloxy)-3,4-dihydroxyhexanediamide N1,N6-di[(1S)-2-methyl-1-(methylcabamoyl)propyl]-(2R,3R,4R,5R)-2,5-di[4-(3-fluorobenzyi)oxy]-3,4-dihydroxyhexanediamide N1,N6-di[(1S,2R)-2-hydroxy-2,3-dihydro-1H-1-indenyl]-(2R,3R,4R,5R)-2,5-di(3-fluorobenzyloxy)-3,4-dihydroxyhexanediamide N1,N6-di[(1S)-2-methyl-1-(methylcarbaroyl)propyl]-(2R,3R,4R,5R)-2,5-di[4-(2-fluorobenzyl)oxy]-3,4-dihydroxyhexanediamide N1,N6-di[(1S)-2-methyl-1-(methylcarbmoyl)propyl]-(2R,3R,4R,5R)-2,5-di[4-(2,4-difluorobenzyl)oxy]-3,4-dihydroxyhexanediamide N1,N6-di[(1S,2R)-2-hydroxy-2,3-dihydro-1H-1-indenyl]-(2R,3R,4R,5R)-2,5-di(2,4-difluorobenzyloxy)-3,4-dihydroxyhexamediamde N1,N6-di[(1S)-2-methyl-1-(methylcarbamoyl)propyl]-(2R,3R,4R,5R)-2,5-di[4-(2-pyridyl)benzyloxy]-3,4-dihydroxyhexanediamde N1,N6-di[(1S)-2-methyl-1-(methylcarbamoyl)propyl]-(2R,3R,4R,5R)-2,5-di[4-(2-pyridyl)benzyloxy]-3,4-dihydroxyhexanediamide N1,N6-di[(1S)-2-methyl-1-(methylcarbarnoyl)propyl]-(2R,3R,4R,5R)-2,5-di[(4-(3-nitrophenyl)benzyl)oxy]-3,4-dihyydroxyhexanediamnide N1,N6-di[(1S)-2-methyl-1-(methylcarbamoyl)propyl]-(2R,3R,4R,5R)-2,5-di[4-(2-thienyl)benzyloxy]-3,4-dihydroxyhexanediamide N1,N6-di[(1S,2R)-2-hydroxy-2,3-dihydro-1H-1-indenyl](2R,3R,5R)-2,5-di(benzyloxy)-3-hydroxyhexanediamide N1-[(1S,2R)-2-hydroxy-2,3-dihydro-1H-1-indenyl]-N6-(2-chloro-6-fluorobenzyl)-(2R,3R,4R,5R,)-2,5-di(2-fluorobenzyloxy)-3,4-dihydroxyhexanediamide, and their pharmaceutically acceptable salts and prodrugs.

O-alkylated dilactone intermediates are also novel compounds and thus a father aspect of the invention provides compounds of the formula IV:

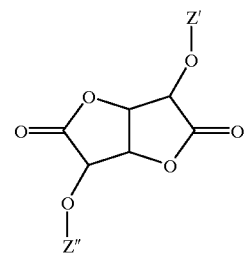

IV where Z' and Z" are as defined above. Preferably the compound of formula IV has the following stereochemistry:

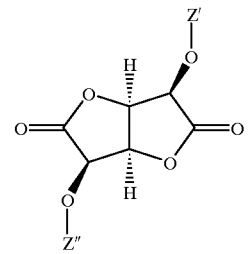

Favoured compounds of formula IV include those where Z' and Z" are benzyl, 2-fluorobenzyl, 2-methylbenzyl, 2,4-difluorobenzyl, 4-fluorobenzyl, 4-bromobenzyl, 4-phenylbenzyl, 4-thiophenylbenzyl, 4-(4'-nitrophenyl)benzyl, 4-(pyridyl)benzyl or benzyl parasubstituted with a pria, secondary or tertiaty amine or an N-bonded heterocycle such as piperidine, morpholine etc. Altetnatives to benzyl for Z' or Z" groups may comprise other arylC$_{1-2}$alkyl or heteroarylC$_{1-2}$alkyl such pyridylmethylene, quinolylmethylene or napthylmetylene as known in the P1 protease art.

As with formula I, the Z' and Z" groups on the compounds of Formula IV may differ, but it is convenient, and consistent with the bimeric nature of the target enzyme if they are the same.

Preferred intermediate compounds of Formula IV thus include:

2,5-di-O-benzyl-L-mannaro-1,4:6,3-dilactone, 2,5-di-O-(2-fluorobenzyl)-L-mannaro-14:6,3-dilactone, 2,5-di-O-(2,4-difluorobenzyl)-L-mannaro-1,4:6,3-dilactone, 2,5-di-O-(4-fluorobenzyl)-L-mannaro-1,4:6,3-di-lactone, 2,5-di-O-(2-chlorobenzyl)-L-mannaro-1,4:6,3-dilactone, 2,5-di-O-(4-chlorobenzyl)-L-mannaro-1,4:6,3-di-lactone, 2,5-di-O-(4-thiophen-3'-yl-benzyl)-L-mannaro-1,4:6,3-di-lactone 2,5-di-O-(4-thiophen-2'-yl-benzyl)-L-mannaro-1,4:6,3-di-lactone, 2,5-di-O-(4-(thiazol-4'-yl)-benzyl)-L-mannaro-1,4:6,3-di-lactone 2,5-di-O-(4-thiazol-2'-yl-benzyl)-L-manaro-1,4:6,3-di-lactone,
2,5-di-O-(4-phenylbenzyl)-L-mannaro-1,4:6,3-di-lactone,
2,5-di-O-(4-phenylbenzyl)-L-mannaro-1,4:6,3-di-lactone,
2,5-di-O-(4-(4'-nitrophenylbenzyl)-L-mannaro-1,4:6,3-di-lactone,
2,5-di-O-(4-(4'-cyanophenylbenzyl)-L-mannaro 1,4:6,3-di-lactone,
2,5-di-O-(4-(4'-halophenylbenzyl)-L-mannaro-1,4:6,3-di-lactone,
2,5-di-O-(4-(4'-aminophenylbenzyl)-L-mannaro-1,4:6,3-di-lactone,
2,5-di-O-(4(4'-carboxyphenytbenzyl)-L-mannaro-1,4:6,3-di-lactone,
2,5-di-O-(4-(4'-phenylbenzyl)-L-niannro-1,4:6,3-di-lactone,
2,5-di-O-(4-pyrid-2-ylbenzyl)-L-mannaro-1,4:6,3-di-lactone,
2,5-di-O-(4-pyrid-3-ylbenzyl)-L-annaro-1,4:6,3-di-lactone,
2,5-di-O-(4-N-morpholinylbenzyl)-L-mannaro-1,4:6,3-di-lactone,
2,5-di-O-(4-N-piperazinylbenzyl)-L-mannaro-1,4:6,3-di-lactone,
2,5-di-O-(4-benzylbenzyl)-L-mannaro-1,4:6,3-di-lactone,
and the like.

Intermediate compounds of formnula III can be prepased by the following reaction scheme:

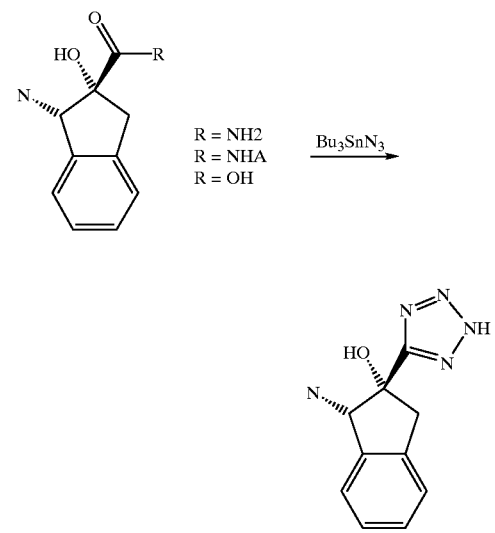

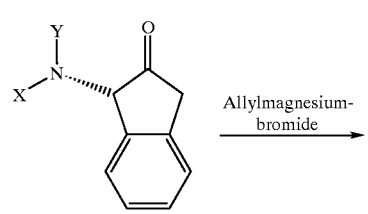

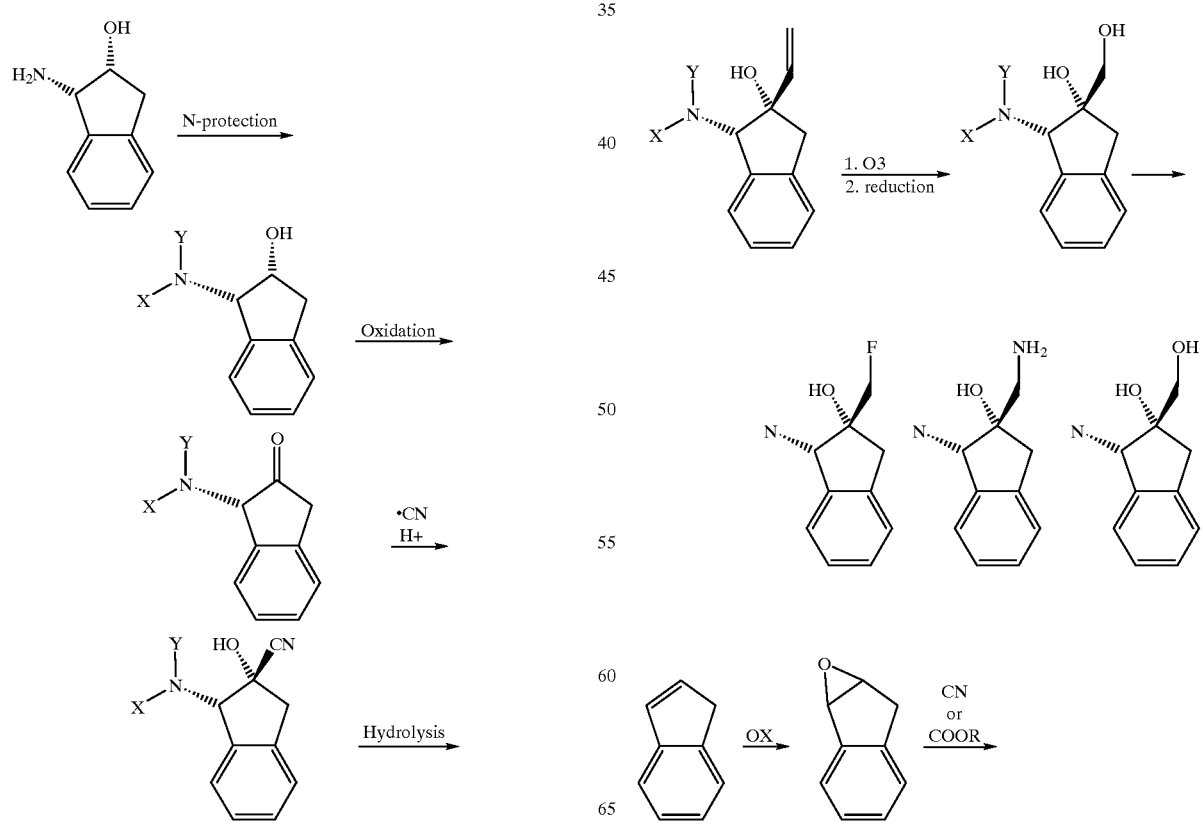

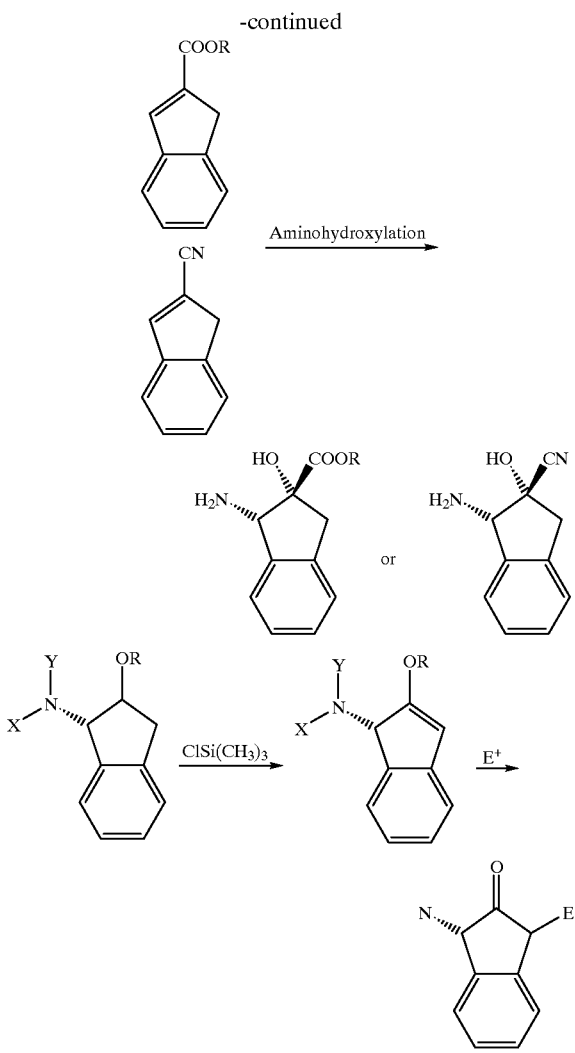

1-amino-azaindan-2-ol P-2 filling groups can be prepared analogously to J Med Chem 1991 1228–1230:

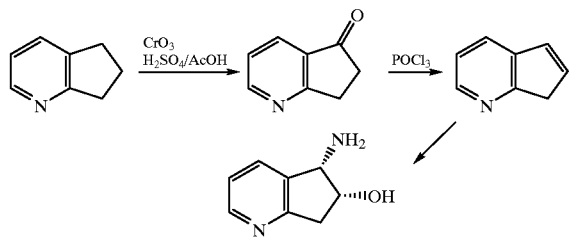

In treating conditions caused by retroviruses, the compounds of formula I are preferably administered in an amount to achieve a plasma level of around 10 to 1000 nM and more preferably 100 to 500 nM. This corresponds to a dosage rate, depending on the bioavailability of the formulation of the order 0.001 to 100 mg/kglday, preferably 10 to 50 mg/kg/day.

In keeping with the usual practice with IRV inhibitors it is advantageous to co-administer one to three additional antivirals, such as AZT, ddI, ddC, D4T, ritonavir, saquinavir, indinavir, nelfinavir, DMP 266, delavirdine, nevirapine, trovirdine, PFA, H2G etc. The molar ratio for such co-administered antivirals will generally be chosen to reflect the respective $EC_{50}$ performances of the antiviral. Molar ratios of 25:1 to 1:25, relative to the compound of formula I will often be convenient.

While it is possible for the active agent to be administered alone, it is preferable to present it as part of a pharmaceutical formulation. Such a formulation will comprise the above defined active agent together with one or more acceptable carriers and optionally other therapeutic ingredients. The carrier(s) must be acceptable in the sense of being compatible with the other ingredients of the formulation and not deleterious to the recipient.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylceflulose, sucrose and starch; fillers and carriers, for example corn starch, gelatin, lactose, sucrose, microcrystalline cellulose, kaolin, mannitol, dicalciuin phosphate, sodium chloride and alginic acid; and lubricants such as magnesium stearate and other metallic stearates, steeic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the arL A tablet may be made by compression or moulding, optionally with one or more accessory ingredients. Compressed tablets may be prepared by compressing in a suitable machine the active agent in a free flowing form such as a powder or granules, optionally mixed with a binder, lubricant inert diluent, preservative, surface-active or dispersing agent. Moulded tablets may be made by moulding in a suitable mrachine a mixture of the powdered compound moistened with an inert liquid diluenl The tablets may be optionally be coated or scored and may be formulated so as to provide slow or controlled release of the active agent.

Formulations suitable for topical administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Formulations suitable for topical administration to the skin may be presented as ointments, creams, gels, and pastes comprising the active agent and a pharmaceutically active carrier. An exemplary topical delivery system is a transdermal patch containing the active agent.

Formulations for rectal or vaginal administration may be presented as a suppository or pessary with a suitable base comprising, for example, cocoa butter or a salicylate. Other vaginal preparations can be presented as tampons, creams, gels, pastes, foams or spray formulations containing, in addition to the active agent, such carriers as are known in the art to be appropriate.

Formulations suitable for nasal administration wherein the carrier is a solid include a coarse powder having a particle size, for example, in the range 20 to 500 microns which is administered in the manner in which snuff is taken, i.e. by rapid inhalation from a container of the powder held up close to the nose. Suitable formulations wherein the carrier is a liquid for administration, for example, as a nasal spray or as nasal drops, include aqueous or oily solutions of the active agent.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freezedried (lyophilized) condition requiring only the addition of the 'sterile liquid carrier, for example water for injection, immediately prior to use. Extemporaneous injection solutions and suspensions may be prepared from sterile powders, granules, and tablets of the kind previously described.

DETAILED DESCRIPTION OF EMBODIMENTS OF THE INVENTION

The invention will now be fmfrfer illustrated by reference to the following non-limiting Examples.

EXAMPLE 1

N1,N6-di[(1S)-2-methyl-1-(methylcarbamoyl) propyl]-(2R,3R,4R,5R)-2,5-di(benzyloxy)-3,4-dihydroxybexanediamide

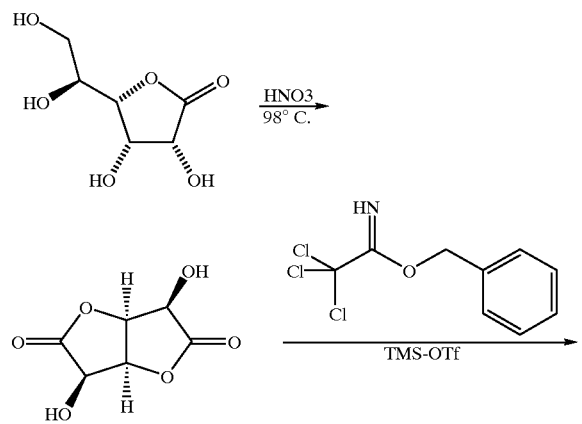

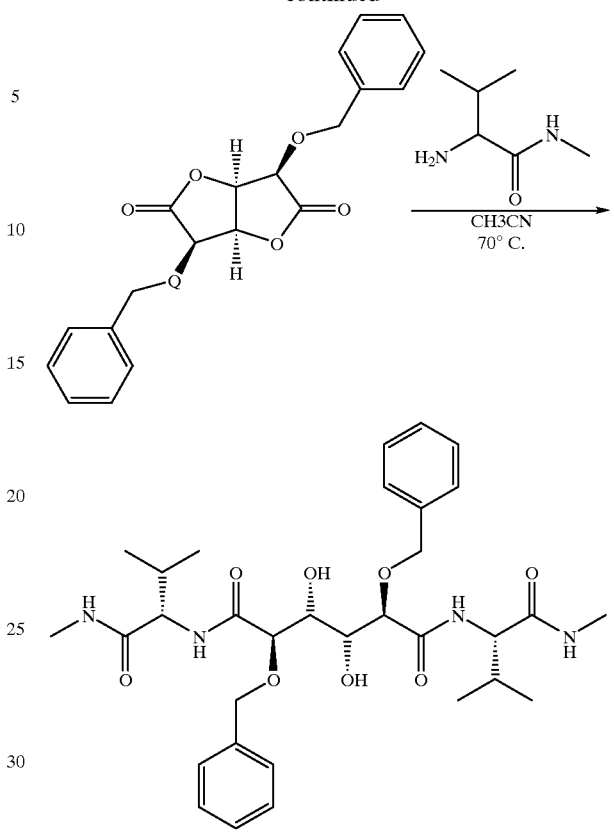

In short, oxidation of L-mannonic-γ-lactone with nitric acid gave crystalline L-mannaric-1,4:6,3-di-lactone which was dibenzylated with dibenzyl trichloroacetimidate and trimethylsilyltriflate to give 2,5-di-O-benzyl-L-mannaric-1, 4:6,3-di-lactone. This lactone may be opened by the addition of any primary or most secondary arnines, in this case by N-methyl-L-valine to give the titled compound in 10–30% overall yield.

In more detail, the above synthesis scheme proceeded as follows:

A. L-mannonic-γ-lactone (8.1 g) in aqueous (65%) $HNO_3$ (120 ml) was kept at 98° C. under a stream of nitrogen for 1–2 hours. After concentration to a sticky mass, water (50 ml) was added and the solution was concentrated to near dryness. This material was dried in a vacuum for 16 hours whereupon ethanol (5 ml) and ether (100 ml) were added and the solid was finely dispersed by sonification and mechanical grinding. The solution was taken off and the solid was washed with ethanol (10 ml). The remaining solid was recrystallised in ethanol to give 4.3 g of L-mannaric-1,4:6,3-di-lactone.

$^{13}$C-NMR (DMSO-d6): δ 69.2 (C2, C5), 75.9 (C3, C4), 174.3 (C1, C6).

B. Trimethylsilyltriflate or trifluoromethylmethanesulphonic acid (44 drops from a Pasteur pipette) was added to a well stirred solution of L-mannaric-1,4:6,3-di-lactone (696 mg) and benzyl trichloroacetimidate (3040 mg) in dioxane (140 ml). After 1.5 hours the solution was filtered trhough a pad of 1 cm silica, 1 cm $NaHCO_3$ and 1 cm silica, washed through with dioxane (20 ml), concentrated to dryness and recrystallised from $CHCl_3$ to give 1.85 of solid. This solid was slurried in hot ether and filtered. The remaining solid (900 mg) was collected as 2,5-di-O-benzyl-L-mannaric-1, 4:6,3-di-lactone.

$^{13}$C-NMR (DMSO-d6): δ 72.3, 74.6, 75.1 (CH$_2$O, C2, C3, C4, C5), 128.2, 128.3, 128.7, 137.2 (Ar), 172 (C1, C6).

C. A solution of 2,5-di-O-benzyl-L-mannaric-1,4:6,3-dilactone (50 mg) and N-methyl-L-valine (110 mg) in acetonitdle (0.5 ml) was kept at 70° C. for 16 hours. After cooling the product was purified by silica gel column chromatography (CHCl$_3$-MeOH 9:1) to (35 mg).

EXAMPLE 2

N1,N6-di[(1S)-2-methyl-1-(methylcarbamoyl)propyl]-(2R,3S,5R)-2,5-di(benzyloxy)-3-hydroxyhexarediamide A Preparation of (2R,3S,4S,5R)-2,5-di(benzyloxy)-3,4-O-isoproylidene-3,4-dihydroxyhexanediacid.

To a solution of 2,5-di-O-benzyl-3,4-O-isopropylidene-L-iditol (1.84 g, 4.57 mmol) in CH$_2$Cl$_2$ (90 ml) was added TEMPO (36 mg, 0.23 mmol), potassium bromide (104 mg, 0.87 mmol), tetrabutylammonium bromide (163 mg, 0.51 mmol) and saturated aqueous sodium hydrogen carbonate (20 ml). The mire was cooled to 0° C. and a solution of sodium hypochlorite (42 ml, 1.2 M, 50.4 mmol) was added over a period of 1.5 hours. After stirring at 0° C. for 30 minutes, the organic layer was separated and washed with NaHCO$_3$ (aq) (3×40 ml) and water (3×40 ml). To the combined water phases EtOH (50 ml) was added and the solution stirred for 30 minutes. EtOAc (100 ml) was then added and the pH of the mixture was brought from 9 to 2 by the addition of H$^+$-Dowex. The Dowex was filtered, the phases were separated and the water phase was extracted with EtOAc (4×100 ml), dried and concetrated under reduced pressure without warming to give (1.40 g, 3.25 mmol, 71%).

$^{13}$C-NMR (CD$_3$OD-acetone-d$_6$ 2:1) δ 27.1 (CH$_3$isoprop), 73.7, 77.4, 78.0 111.0 (isoprop), 128.8, 129.1, 129.3 and 138.6 (aromatic C), 172.7 (COOH).

B Preparation of N1,N6-di[(1S)-2-methyl-1-(methylcarbamoyl)propyl]-(2R,3S,4S,5R)-2,5-di(benzyloxy)-34,-O-isopropyidene-3,4-dihydroxyhexanediamide.

The resultant crude product from step A (1.40 g, 3.25 mmol) was dissolved in dry CH$_3$CN (21 ml) under argon and pyridine (1.58 ml, 19.5 mmol) and di-N-succinylimidyl carbonate (DSC) (3.30 g, 12.9 mmol) was added. The mixture was stirred at room temperature for 15 hours, diluted with EtOAc (50 ml), washed with water (3×20 ml) and brine (1×30 ml), dried, concentrated and purified by silica gel column chromatography.

The activated diacid from above (974 mg, 1.64 mmol) was dissolved in a 2:1 mixture of CH$_2$Cl$_2$-THF (7 ml) under argon and L-valine methylamide (560 mg, 4.30 mmol) was added. The reaction was stirred at room temperature for 18 hours, diluted with CH$_2$Cl$_2$ (50 ml) and washed with NH$_4$Cl (aq) (30 ml). The organic layer was dried, concentrated and purified by silica gel column chromatography (CHCl$_3$-MeOH 20:1) to yield 844 mg, 1.29 mmol, 79%.

$^{13}$C-NMR (CDCl$_3$): δ 16.7 and 19.7 (val CH$_3$), 26.2 (val CH$_3$NH), 27.2 (CH$_3$ isoprop), 28.9 (val CHMe$_2$), 57.8 (val CHNH), 73.7, 77.1, 77.0, 110.0 (isoprop), 128.2, 128.4, 128.7, 129.0 and 135.7 (aromatic C), 169.8 and 170.9 (CONH and val CO).

C Preparation of N1,N6-di[(1S)-2-metbyl-1-(methylcaribamoyl)propyl]-(2R,3S,4S,5R)-2,5-di(benzyloxy)-3,4-dihydroxyhexanediamide.

The product from step B (775 mg, 1.18 mmol) was dissolved in a 5:1 mixture of CH$_3$CN-H$_2$O (309 ml), 2,3-dichloro-5,6-dicyanobenzoquinone (DDQ) (30 mg, 0.13 mmol) was added and the temperature was kept at 75° C.

After 2 days and 4 days additional portions (2×60 mg) of DDQ were added and after 6 days the reaction was concentrated. The residue s dissolved in EtOAc (50 ml), washed with water (2×30 ml), filtered through a pad of arcoal, celite and Na$_2$SO$_4$ and puwified by silica gel column chromatography(CHCl$_3$-MeOH 20:1) to give (501 mg, 0.81 mmol, 69%). [α]$_D$ −22.9° (c 1.4 g/100 ml CHCl$_3$).

$^{13}$C-NMR (CDCl$_3$): δ 16.7 and 19.7 (val CH$_3$), 26.2 (val CH$_3$NH), 28.6 (val CHNH), 57.7 (val CHNH), 69.6, 73.7, 77.6; 128.2, 128.9 and 135.9 (aromatic C), 170.8 and 172.3 (CONH and val CO). anal calcd. For C$_{32}$H$_{46}$N$_4$O$_8$: C 62.52; H 7.54; N 9.11. Found C 62.41; H 7.39; N 8.98.

D Preparation of N1,N6-di[(1S)-2-methyl-1-(methylcarbarnoyl)propyl]-(2R,3S,5R)-2,5-di(benzyloxy)-3-hydroxyhexanediamide.

The product from step C (58 mg, 94 μmol) was dissolved in dry THF (5 ml) under an argon atmosphere and heated to 45° C. before N,N-thiocarbonyldiimidazle (40 mg, 0.22 mmol) was added The reaction mixture was refluxed for 30 hours, concentrated and purified by silica gel column chromatography (chloroform-methanol 20:1) to give the thiocarbonate (60 mg, 91 μmol, 97%)

$^{13}$C-NMR (CDCl$_3$): δ 17.2 and 195 (val CH$_3$), 26.4 (val CH$_3$NH), 29.7 (val CHMe$_2$), 58.7 (val CHNH), 75.6, 78.0, 83.4, 128.3, 128.9 and 135.2 (aromatic C), 167.7 and 170.6 (CONH and val CO), 189.6 CS).

A suspension of the thiocarbonate (60 mg, 91 μmol), tributylin hydride (50 μl, 0.19 mmol) and α,α'-azaisobutyronitrile (15 mg, 91 μmol) in dry toluene (4 ml) was added dropwise to refluxing toluene (2 ml) over a period of 20 minutes. The mnixture was refluxed for 45 minutes, allowed to cool and concentrated. The residue was dissolved in acetonitrile (10 ml) and washed with hexane (2×5 m). The acetonitrile layer was concentrated and purified by silica gel column chromatography (toluene-acetone 1:1) to give the titled product in 33% yield (18 mg, 30 μmol). [α]$_D$ +6.1° (c 0.7 g/100 ml CHCl$_3$).

$^{13}$C-NMR (CDCl$_3$): δ 17.3, 17.4 and 19.6 (val CH$_3$), 26.3 (val NHCH$_3$), 29.5 (val CHMe$_2$), 34.5 ( ) 58.0, and 58.1 (val CHNH), 68,5, 72.7, 73.7, 76.8, 81.1, ( ), 127.9, 128.3, 128.5, 128.6, 128.8, 136.2 and 136.5 (aromatic C), 171.1, 171.4, 171.6, and 172.5 (NHCO and val CO).

EXAMPLE 3

N1,N6-di[(1S)-2-methyl-1-(methylcarbmoyl)propyl]-(2R,3R,5R)-2,5-dibenzyloxy)-3-hydroxyhexanediamide The product of Example 1 (144 mg, 0.23 mmol) was dissolved in dry THF (8 ml) under an argon atmosphere and heated to 45° C. before N,N-thiocarbonyldiimidazole (104 mg, 0.58 mmol) was added. The reaction mixture was refluxed for 17 hours, concentrated and punfied by silica gel column chromatography (chloroform-methaol 20:1) to give the thiocarbonate (125 mg, 0.19 mmol, 83%).

$^{13}$C-NMR (CDCl$_3$): δ 17.4 and 19.4 (val CH$_3$), 26.3 (val CH$_3$NH), 30.2 (val CHMe$_2$), 58.4 (val CHNH), 75.8, 77.7, 82.4 ( ), 128.9, 129.1 and 135.3 (aromatic C), 167.0 and 170.6 (CONH and val CO)m 190.7 (CS).

The thiocarbonate (125 mg, 0.19 mmol) was suspended in dry toluene (4 ml) under an argon atmosphere and heated to reflux, and a solution of tributylin hydride (153 μl, 0.57 mmol) and α,α-azaisobutyronitrile (47 mg, 0.28 mmol) in dry toluene (3 ml) was added over a period of 10 minutes. The mixture was refluxed for 20 hours, allowed to cool and concentrated. The residue was dissolved in acetonitrile (15 ml) and washed with hexane (2×30 10 ml). The acetonitrile layer was concentrated and purified by silica gel column chromatography (CHCl$_3$-MeOH 20:1) to give the titled product in 35% yield (40 mg, 67 μmol). [α]$_D$+1.8° (c 0.8 g/100 ml CHCl$_3$).

$^{13}$C-NMR (CDCl$_3$): δ 17.5, 18.0, 19.4 and 19.6 (val CH$_3$), 26.1 and 26.3 (val CH$_3$NH), 295 and 30.6 (val CHMe2), 35.5, 58.2, 58.3, (val CHNH), 70.2, 73.0, 73.3, 77.2, 83.0, 127.9, 128.0, 128.4, 128.6, 136.7, (aromatic C), 170.5, 1713, 121.4, 173.1 (CONH and val CO). Anal calcd. For C$_{32}$H$_{46}$N$_4$O$_7$: C 64.19; H 7.74; N 9.36; Found: C 64.00; H 7.50; N 9.15.

EXAMPLE 4

N1,N6-di[(1S)-2-methyl-1-(methylcarbamoyl) butyl]-(2R,3R,4R,5R)-2,5-di(benzyloxy)-3,4-dihydroxyhexanediamide A soluton of 2,5di-O-benzyl-L-mannaric-1,4:6,3-di-lactone from Example 1 (50 mg) and N-methyl-L-isoleucine (120 mg) in acetonitrble was maintained at 70° C. for 16 hours. After cooling the product was purified by silica gel column chromatography (CHCl$_3$-MeOH 19:1) to give the pure compound.

$^{13}$C-NMR (CD$_3$OD) δ 11.7, 16.1, 25.1, 26.3, 37.2, 58.5, 72.3,73.4, 80.8, 128.7, 129.1, 137.7, 72.7, 173.1.

EXAMPLE 5

N1,N6-di[(1S)-1-(methylcarbamoyl)-2-phenylethyl]-(2R,3R,4R,5R)-2,5-di(benzyloxy)-3,4-dihydroxyhexanediamide 2,5-di-O-benzyl-L-mannaric-1,4:6,3-di -lactone from Example 1 (30 mg, 0.085 mmol) was dissolved in dichloromethane (3 ml) and phenylalanine-N-methylamide (91 mg, 0.51 mmol) was added to the stirred solution. The solution was refluxed (40° C.) for 18 hours and then concentrated. The crude product was purified by silica gel column chromatography (chloroform-methanol 20:1).

$^{13}$C-NMR (CD$_3$OD) δ 72.8, 73.7, 81.9, 127.1, 127.8, 128.4, 128.7, 128.8, 129.0, 135.0, 136.4, 170.0, 172.1.

EXAMPLE 6

N1,N6-di[(1S)-1-(methylcarbamoyl)-2-(4-hydroxyphenyl)ethyl]-(2R,3R,4R,5R)-2,5-di(benzyloxy)-3,4-dihydroxhexanediamide 2,5-di-O-benzyl-L-mannaric-1,4:6,3-di-lactone from Example 1(40 mg, 0.113 mmol) was dissolved in dichloromethane (4 ml) and tyrosine N-methylamide (132.2 mg, 0.677 mmol) was added to the stirred solution. The solution was refluxed (40° C.) for 18 hours and concentrated The crude product was purified by silica gel column chromatography (chloroform-methanol 20:1).

$^{13}$C-NMR (CD$_3$OD) δ 26.1, 37.1, 55.3, 72.9, 72.9, 81.1, 116.1, 128.8, 129.2, 130.9, 138.3, 157.2, 172.9, 173.6.

EXAMPLE 7

N1,N6-di[(1S)-2-methyl-1-(methylcarbamoyl) propyl]-(2R,3R,4R,5R)-2,5-di[(4-fluorobenzyl)oxy]-3,4-dihydroxyhexanediamide A To a cooled (-10C) solution of 4-fluorobenzyl alcohol (0.85 ml, δ 1.168 g/ml, 7.93 mmol, leq) in CH$_2$Cl$_2$ (10 ml) and KOH (50% aq. 10 ml) was added tetrabutylannronium hydrogen sulphate (0.015 g). After stirring for 5 minutes, tfichloroacetonitrile (0.953 ml, c 1.44 g/ml, 9.51 mmol, 1.2 eq) was added and the reaction mixture maintained at -5° C. for 30 minutes before warming to room temperature. The organic phase was separated and the water phase extracted with CH$_2$Cl$_2$ (2×10 ml). The combined extracts were dried with MgSO$_4$ and concentrated to one third. After filtration through Celite the solvent was removed in vacuo to give the dilactone as a brownish-yellow oil, 1.82 g (85% yield).

$^1$H-NMR (CHCl$_3$ 250 MHz) δ 5.30 (s, 2H), 7.00–7.15 (m, 2H), 7.40 (m, 2H), 8.40 (b, 1H).

B Preparation of 2,5-di-O-(4fluorobenzyl)-L-mannaro-1,4:6,3-di-lactone.

To a solution of the dilactone from step A (0.200 g, 1.12 mmol) in dioxane (40 ml) was added 4-fluorbenzyl trichloroacetimidate (0.72 g, c 1.353 g/ml 3.37 mmol, 3 eq). The reaction vessel was placed under a N$_2$(g) atmosphere and stirred (10 min). TMS-OTf (0.08 ml, c 1.230 g/ml, 0.45 mmol, 0.4 eq) was added portionwise. After 4 hours the mixture was filtered through a pad of SiO$_2$-NaHCO$_3$-SiO$_2$, recrystallised from CHCl$_3$, slurried with Et$_2$O (2 ml) and filtered to give (0.315 g, 71.8% yield).

$^1$H-NMR (DMSO-d$_6$, 250 MHz) δ 4.75, 4.80 (d, J=7.1 Hz, 4H), 4.90 (d, J=3.7 Hz, 2H), 5.3 (d, J=5.8 Hz, 2H), 7.15–7.25 (m, 4H, 7.40–7.55 (m, 4H). $^{13}$C-NMR (DMSO-d$_6$ 62.9 MHz) δ 71.4, 74.4, 74.7, 115.1, 115.5, 130.2, 130.3, 133.3, 160.0, 164.0, 171.8.

C To the benzylated di-lactone from above (0.050 g, 0.128 mmol, 1.0 eq) in CH$_3$CN (pa, 2 ml) was added L-valne-N-methylamide (0.050 g, 3.84 mmol, 3.0 eq). The reaction mixture was heated to 70° C. and stired for 24 hours. Concentration gave a brown oil (crude 0.107 g). purification by silica gel flash chromatography (9:1 CHCl$_3$: MeOH) (12:1 CHCl$_3$. MeOH+1% HOAc) and (12:1 CHCl$_3$: MeOH) to give 0.006 g of the titled product (yield 7.2%).

$^1$H-NMR (DMSO-d$_6$, 250 MHz) δ 0.90–0.95 (m, 6H), 1.90–2.05 (m, 2H), 2.55 (m, 6H), 3.80–3.90 (m, 2H), 3.95–4.05 (d, J=7.8 Hz), 2H), 4.10–4.20 (m, 2H), 4.40–4.45 (m, 4H), 4.75–4.65 (d, J=7.47 Hz, 2H), 7.10–7.20 (m, 4H), 7.25–7.40 (m, 4H), 7.75–7.80 (d, J=8.94 Hz, 2H), 7.85–7.90 (d, J=4.64 Hz, 2H). $^{13}$C-NMR (DMSO-d$_6$ 62.9 MHz) δ 18.0, 19.1, 25.3, 57.5, 69.6, 70.26, 79.2, 93.0, 114.7, 115.0, 129.5, 129.6, 134.1, 159.5, 163.4, 170.3, 171.0, 115.1, 115.5, 130.2, 130.3, 133.3, 160.0, 164.0, 171.8.

EXAMPLE 8

N1,N6-di[(1S)2-methyl-1-(cyclopropylcarbamoyl) propyl]-(2R,3R,4R,5R)-2,5-di(benzyloxy)-3,4-dihydroxyhexanediamide An analogous procedure to Example 2B but using L-valine-N-cyclopropylaride (117 mg, a0.27 mmol) yielded the corresponding intermediate as an off-white solid (147 mg, 0.25 mmol, 93%).

$^{13}$C NMR (CDCl$_3$): δ 6.1, 6.7 (CH$_2$ cyclopropyl), 17.4, 19.4 (val CH$_3$), 22.6 (val CHMe$_2$), 27.1 (CH$_3$ isoprop), 30.1 (CHNH-cyclopropyl), 57.8 (NHCH), 74.2 (C3, C4), 76.6 (C2, C5), 78.9 (OCH$_2$Ph), 110.3 (isoprop), 128.4, 128.7, 128.9, 136.5 (arom C), 169.3 (val C=O), 172.1 (NHC=O).

This intermediate (86 mg, 0.16 mmol) was subjected to the procedure of Example 2C to yield the titled compound (52 mg, 0.010 mmol, 65%) as an off-white solid. [α]$_D$-17° (c. 0.86 CHCl$_3$).

$^{13}$C-NMR (CDCl$_3$): δ 5.8, 6.3 (CH$_2$-cyclopropyl), 16.8, 19.5 (val CH3), 22.8 (val CHMe$_2$), 28.9 (CHNH-cyclopropyl), 58.0 (NHCH), 73.4 (C3, C4), 73.4 (C2, C5), 82.2 (OCH$_2$Ph), 128.6, 128.8, 129.3, 136.2 (arom C), 171.1 (val C=O), (172 NHC=O).

EXAMPLE 9

N1,N6-di[[(1S)-2-methyl-1-(methlcarbamoyl) propyl]-(2R,3R,4R,5R)-2,5-di[(2-methylbenzyl) oxy]-3,4-dihydroxyhexanediamide A 1,6-di-(dimethyl-tert-butylsilyl)-3,4-O-isopropyl-L-mannitol (1.834 g, 4.07 mmol) was dissolved in dry tetrahydrofuran (25 ml). The solution was then cooled to 0° C. and sodium hydroxide (60% aq. 0.556 g, 13.44 mmol, 33 eq) was added. The cooling bath was removed and the reaction stirred at room temperate for 15 minutes. 2-Methylbenzyl bromide (120 ml, 8.96 mmol 2.2 eq) and tetrabutylammonium iodide (0.285 g, 0.77 mmol, 0.19 eq) were added and the reaction mixture stirred at room temperature overnight. The solution was then diluted with diethyl ether (200 ml) and washed three times with water (200 ml). The organic phase was dried and concentrated. The product was purified by silica get flash chromatography (toluene) to give the disilyl ether (1.86 g, 70%).

$^1$H-NMR (CDCl$_3$ 250 MHz) δ 0.10 (s, 12H, 2×CH$_3$C[CH$_3$]$_2$-Si), 0.090 (s, 12H, 2×[CH$_3$]$_2$-Si), 130 (s, 6H, 2×CH$_3$C[CH$_3$]$_2$Si), 1.40 (s, 6H, 2×isoprop, CH$_3$), 2.30 (s, 6H, 2×Ph—CH$_3$), 3.63–3.78 (m, 4H, H-1, H-6), 3.86–3.94 (dd, 2H, H-2, H-5, J=7.47, 3.20 Hz), 4.17–4.24 (dd, 2H, H-3, h4, J=1.72, 1.29 Hz), 4.50–4.82 (dd, 4H, 2×O-CH$_2$-Ph, J=52.55, 11.86 Hz), 7.08–7.36 (m, 8H, 2×Ph). $^{13}$C-NMR (CDCl$_3$ 62.9 MHz): δ 5.47 ([CH$_3$]$_2$-Si), 18.61 (CH$_3$C[CH$_3$]$_2$-Si), 25.90 (2×CH$_3$C[CH$_3$]$_2$-Si), 27.25 (isoprop.C), 29.72 (2×Ph—CH$_3$), 63.70 (C-1, C-6), 71.38 (C-2, C-5), 78.29 (2×O-CH$_2$-Ph), 81.47 (C-3, C4), 109.49 (isoprop.C) 125.65, 127.42, 128.32, 129.31 (2×Pb).

B Preparation of 2,5-di-O-(2-methylbenzyl)-3,4-isopropylidene-L-mannitol

The disilyl ether from step A (1.749 g, 2.65 mmol) was dissolved in dry tetrahydrofuran.

Tetrabutylammoniumfluoride in THF (6.92 ml, 1.0 M, 2.6 eq) was added. The solution was stirred at room temperature for 2.5 hours and concentrated. The product was purified by silica gel flash chromatography (toluene: ethyl acetate 1:1) to give the titled diol (0.99 g, 88%).

$^1$H-NMR (CDCl$_3$, 250 MHz) δ 1,40 (s, 6H, 2×isoprop.CH$_3$), 2.35 (s, 6H, 2×Ph—CH$_3$), 3.60–3.68 (m, 4H, H-1, H-6), 3.75–3.85 (m, 2H, H-2, H-5), 4.19–4.25 (dd, 2H, H-3, H-4, J=2.40, 1.35 Hz), 4.52–4.71 (dd, 4H, Ph—CH$_2$-O, J=13.49, 11.58 Hz), 7.10–7.25 (m, 8H, 2×Ph). $^{13}$C-NMR (CDCl$_3$ 62.9 MHz) δ 61.26 (C-2, C-5), 70.68 (C-1, C-6), 78.95 (2×O—CH$_2$—Ph). 80.94 (C-3, C-4), 125.92, 127.47, 128.69, 129.32 (2×Ph).

C Preparation of 2,5 -di-O-(2-methylbenzyl)-isopropylidene-L-mannaric acid

To the diol from step B (0.126 g, 0.51 mmol) in dichloromethane (3.6 ml) was added 2,2,6,6-tetrarethylpiperidin-1-yloxyl, free radical (0.003 g, 0.02 mmol, 0.03 eq) and a solution of potassium bromide (0.006 g, 0.05 mmol, 0.09 eq) and tetramethylammonium bromide (0.008 g, 0.03 mmol, 0.05 eq) and saturated aqueous sodium hydrogen carbonate (2.20 ml) was added. This solution was cooled to 0° C. and a solution of sodium hypochlorite (14%, 4.32 ml, 10.2 mmol, 20 eq), saturated aqueous sodium chlorite (2.30 ml) and saturated aqueous sodiun hydrogencarbonate (1.20 ml) was added over 45 minutes. After stirring for an additional 1 hour the organic phase was washed with 3×15 ml H$_2$O and the combined water phases were acidified with 1M hydrochloric acid to pH 2. The acid aqueous phase was then washed three times with ethyl acetate (15 ml), the organic phase was dried and concentrated to give the titles diacid. The product could be used directly in the next step.

D (i) Preparation of N-(benzyloxycarbonyl)-N'-methyl-L-valinamide

Cbz-valine (2.55 g, 10.17 mmol), methylamine hydrochloride (0.824 g, 12.20 mmol, 1.2 eq) and 1-hydroxybenzotriazole (2.06 g, 15.25 mmol, 1.5 eq) was dissolved in dichloromethane (125 ml) and triethyl amine (5.52 ml, 39.65 mmol, 3.9 eq) was added to adjust the pH to 7.5. The solution was cooled to 0° C. and N,N'-dicyclohexylcarbodimiide (2.94 g, 14.24 mmol, 1.4 eq) was added and the solution was stirred for an additional 1 hour in a cooling bath. The solution was then stirred overnight at room temperature. The reaction was filtered, concentrated and dissolved in ethyl acetate (176 ml). The organic phase was washed with water (125 ml) and sodium hydrogen carbonate (125 ml) dried and concentrated. The product was purified by recrystallization in ethyl acetate-hexane to give the titled product (2.04 g, 75%).

$^1$H-NMR (CDCl$_3$, 250 MHz) δ 0.90–1.00 (m, 6H, [CH$_3$]$_2$CH—CH), 1.66 (s, 1H, CH—CH[CH$_3$]$_2$), 3.80 (d, 3H, J=4.82 Hz), 3.88–3.99 (m, 1H, H-3), 5.10 (s, 2H, H-5), 5.25 –5.41 (d, 1H, NH—CO, J=7.67 MHz), 5.90–6.05 (s, 1H, NH—COO), 7.30–7.42 (m, 5H, Ph). $^{13}$C-NMR (ClCl$_3$, 69.2 MHz) δ 19.24 (C-1), 26.14 (CH—CH[CH$_3$]$_2$), 30.67 (CH—CH-[CH$_3$]$_2$), 60.67 (C-3), 67.06 (C-5), 128.02, 128.20, 128.54, 136.19 (Ph), 156.45 (C-2), 171.80 (C-4).

D (ii) Preparation of N-methyl-valinanide

N-(benzyloxycarbonyl)-N'-methyl-L-valinamide from step (i) above (2.49 g, 9.42 mmol) was dissolved in ethanol (100 ml) and palladium on activated carbon (10%, 0.399 g) was added. The mixture was then hydrogenated (ca. 230 ml H$_2$) at room temperature overnight. The Pd/C was then filtered through a pad of Celite and concentrated. The product was purified with silica gel flash chromatography (dichloromethane-acetone 1:1) to give N-methyl-valinamide (0.870 g, 71%).

$^1$H-NMR (CDCl$_3$, 250 MHz) δ 0.79–0.85 (m, 6H, CH—CH[CH$_3$]2), 1.76 (m, 1H, CH—CH[CH$_3$]$_2$), 2.74–2.76 (d, 2H, H-1, J=4.99 Hz), 3.75–3.77 (d, 1H, H-3, J=4.43), 6.67 (s, 2H, NH$_2$), 7.26 (s, 1H, NH—CH$_3$), $^{13}$C-NMR (CDCl$_3$, 69.2 MHz) δ 19.68 (C-1), 26.23 (CH—CH [CH$_3$]$_2$), 30.77 (CH—CH—[CH$_3$]$_2$), 60.21 (C-3), 166.10 (C-2).

D (iii) Preparation of N1,N6-di[[(1S)-2-methyl-1-(methylcarbamoyl)propyl]-(2R,3R,4R,5R)-3,4-O-isopropylidene-2,5-di[(2-methylbenzyl)oxy]-3,4-dihydroxyhexanediamide.

The diacid of step C (0.247 g, 0.56mmol) and the amide of step D (ii) (0.211 g, 1.62 mmol, 2.9 eq) were dissolved, together with 1-hydroxybenzotriazole (0.270 g, 2.00 mmol, 3.6 eq) in dichloromethane (5.8 ml) and tetrahydrofuran (2.9 ml). Triethylamine (0.18 ml, 1.28 mmol, 2.3 eq) was added to adjust the pH to 7.5. The reaction mixture was cooled to 0° C. and 1-(3-dimethylaminopropyl)-3-ethylcarbodiimide hydrochloride (0.287 g, 1.50 mmol, 2.7 eq) was added and the solution stirred in a cooling bath for 1 hour. The reaction mixture was then stirred for an additional 2 hours at room temperature. The reaction was then diluted with dichloromethane (30 ml) and washed with 3×30 ml sodium hydrogencarbonate, dried and concentrated. The product was purified by silica gel column chromatography (dichloromethane-methanol, 3:1) to give the titled diamide (0.291 g).

1H-NMR (DMSOd$_6$, 250 MHz) δ 0.78–0.94 (m, 12H, 2×(H—CH[CH$_3$]$_2$), 1.22 (s, 6H, isoprop.CH$_3$), 1.87–1.93 (m, 2H, H-4, H-13), 2.24 (s, 6H, 2×Ph—CH$_3$), 2.56 (d, 6H, H-1, H-16, J=4.38 Hz), 4.11–4.14 (m, 6H, 2×CH—CH [CH$_3$]$_2$, H-7, H-8, H-9, H-10), 4.46–4.50 (d, 4H, Ph—CH$_2$-O, J=9.92), 6.48–7.05 (m, 8H, Ph), 7.70–7.75 (d, 2H, 2×CH—NH—CO, J=11.32 Hz), 8.00 (d, 2H, 2×CH$_3$—NH, J=4.44).

E Preparation of N1,N6-di[(1S)2-methyl-1-(methylcarbamoyl)propyl]-(2R,3R,4R,5R)-2,5-di[(2-methylbenzyl)oxy]-3,4-dihydroxyhexanediamide. Hydrochloric acid, 45 in methanol (2 ml) was added to the diamine end product of step D (0.060 g, 0.090 mmol) The reaction mixture was stirred at room temperature for 60 minutes and then concentrated. The product was purified by silica gel column chromatography (dichloromethane: methanol 9:1) to give the titled diamine (0.042 g 74%).

1H-NMR (DMSO-$d_6$, 250 MHz) δ 0.82–0.87, (t, 12H, 2×CH—CH[$CH_3$]$_2$, J=6.06), 1.94–2.02 (m, 2H, CH—CH[$CH_3$]$_2$), 2.25 (s, 6H, 2×Ph—$CH_3$), 2.60 (d, 6H, H-1, H-16, J=4.42), 3.86–3.88 (m, 2H, H-4, H-13), 4.01–4.04 (d, 2H, H-8, H-9, J=7.27), 4.18–4.19 (m, 2H, H-7, H-10), 4.47 (s, 4H, Ph—$CH_2$—O), 7.15–7.31 (m, 8H, Ph), 7.70–7.74 (d, 2H, 2×CH—NH—CO, J=8.82), 7.90–7.92 (d, 2H, 2×$CH_3$—NH, J=4.49). $^{13}$C-NMR (DMSO-$d_6$, 69.2 MHz) δ 17.99 CH—CH[$CH_3$]$_2$, 19.13 (Ph—$CH_3$), 25.31 (CH—CH[$CH_3$]$_2$), 30.40 (C-1, C-16), 57.57 (C-4, C-13), 69.37 (Ph-$CH_2$—O), 69.80 (C-7, C-10), 79.29 (C-8, C-9), 125.47, 127.59, 128.30, 129.78, 131.48, 136.42 (Ph), 170.38 (C-3, C-14), 172.03 (C-6, C-11).

EXAMPLE 10

N1,N6-di[(1S,2R)-2-hydroxy-2,3-dihydro-1H-1-indenyl]-(2R,3R,4R,5R)-2,5-di(benzyloxy)-3,4-dihydroxyhexanediamide 0.915 g (2.2 eq., mmol) of (1S,2R)-1-amino-2-indanol was suspended in 12 ml $CHCl_3$ and heated to 45° C. 2,5-di-O-benzyl-L-mannaric-1,4:6,3-di-lactone (1.0 g, 1.0 eq., 2.82 mmol) from Example 1 was added all at once and stirring was continued at 50° C. during 4 h. Subsequently, the reaction mixture was extracted with saturated aqueous $NH_4Cl$ (2×) and water (2×), dried with $MgSO_4$ and concentrated. Recrystallization from methanol gave (0.65 g, 35%) as a white solid.

$^{13}$C NMR ($CDCl_3$) δ 39.2, 57.8, 71.6, 72.5, 73.5, 81.5, 124.0, 125.3, 127.0, 128.2, 128.3, 128.6, 136.7, 139.8, 140.8, 171.6. Anal. ($C_{38}H_{40}N_2O_8$) C, H, N. [α]$_D$–20.7 (c 0.68, $CHCl_3$).

EXAMPLE 11

N1-[(1S,2R)-2-hydroxy-2,3-dihydro-1H-1-indenyl]-N6-[(1S)-2-methyl-1-(methylcarbamoyl)propyl]-(2R,3R,4R,5R,)-2,5-dibenzyloxy)-3,4-dihydroxyhexanediamide 208 mg (1.0 eq. 1.41 mmol) of (1S,2R)-1-amino-2-indanol was suspended in 4 ml $CH_3CN$ and heated to 55° C. 2,5-Di-O-benzyl-L-mannaric-1,4:6,3-di-lactone (0.5 g, 1.0 eq., 1.41 mmol) from Example 1 was added all at once and stirring was continued at 50° C. during 1.5 h together with 1 ml $CH_3CN$. After 3.5 h another portion of L-valine methylamide (184 mg, 1.0 eq. 1 41 mmol) was added. After 22 h the mixture was concentrated and purified with silica gel flash chromatography ($CHCl_3$-MeOH 30:1; $CHCl_3$-MeOH 20:1 and EtOAc-MeOH 10:1) to give (14 mg, 1.6%).

$^{13}$C NMR ($CDCl_3$) δ 17.2, 19.5, 39.3, 58.0, 58.4, 72.2, 72.4, 72.8, 73.4, 81.4, 81.8, 123.9, 125.4, 127.0, 128.1, 128.2, 128.4, 128.5, 128.7, 128.8, 136.4, 139.6, 140.8, 170.9, 172.0.

EXAMPLE 12

N1,N6-di[(1S,2R)-2-hydroxy-2,3-dihydro-1H-1-indenyl]-(2R,3R,4R,5R)-2,5-di(2-fluorobenzyoloxy)-3,4-dihydroxyhexanediamide A Preparation of 2-fluorobenzyl trichloroacetirnidate.
Procedure as described in Example 7A but using 2-fluorobenzylalcohol gave (2.79 g, 74%).

$^1$H-NMR ($CDCL_3$, 250 MHz) δ 5.36 (s, 2H, H-4), 7.23–7.49 (m, 6H, Ph), 8.45 (s, 1H, NH) $^{13}$C-NMR ($CDCL_3$, 62.9 MHz) δ 64.65 (C-4), 91.14 (C-1), 115.14, 115.45, 123.97, 128.90, 129.97, 130.11 (Ph), 162.18 (C-2).

B Preparation of 2,5di-O-(2-fluorobenzyl)-L-mannaric-1,4:6,3-dilactone.
Procedure as described in Example 7B but using 2-fluorobenzyl trichloroacetimidate gave (0.303 g, 73%) as a white solid.

$^1$H-NMR (DMSO-$d_6$, 250 MHz) δ 4.83 (d, 4H, 2×Ph—$CH_2$, J=8.00), 4.93 (d, 2H, H-3, H-4, J=3.72), 5.31 (d, 2H, H-2, H-5, J=3.78), 7.19–7.54 (m, 8H, 2×Ph) $^{13}$C-NMR (DMSO-$d_6$, 62.9 MHz) δ 65.78 (C-3,C-4), 74.22 (C-2, C-5), 74.95 (2×Ph—$CH_2$), 115.04, 115.37, 124.41, 130.25, 130.38, 130.58 (2×Ph), 170.41 (C-1, C-6).

C Prepared by the procedure as described in Example 10 but using 2,5-di-O-(2-fluorobenzyl)-L-mannaric-1,4:6,3-dilactone gave the tide compound (0.056 g, 33%).

$^1$H-NMR (DMSO-$d_6$, 250 MHz) δ 2.77–3.11 (d+dd, 4H, H-1, H-14, J=4.58, 11.56, 16.07), 3.96 (t, 2H, H-3, H-12, J=7.28), 4.16 (d, 2H, H-7, H-8, J=7.69), 4,44 (q, 2H, H-6, H-9, J=3.83, 4.43), 4.62 (d, 4H, 2×Ph—$CH_2$; J=3.40), 4.92 (d 2H, 2×OH—CH, J=7.23), 5.08 (d, 2H, $CH_2$—OH, J=4.10), 5.27 (q, 2H, C-2, C-13, J=3.61, 5.53), 7.11–7.51 (m, 16H, 4×Ph), 7.82 (d, 2H, NH, J=8.72) $^{13}$C-NMR (DMSO-$d_6$, 62.9 MHz) δ 54.79 (C-1, C-14), 56.57 (C-3, C-12), 64.88 (2×Ph—$CH_2$), 69.81 (C-7, C-8), 72.01 (C-2, C-13), 79.53 (C-6, C-9), 114.80, 115.15, 124.18, 125.70, 124.91, 126.09, 127.16, 129.5, 129.68, 130.10, 140.55, 141.90, 157.86, 161.76 (4—Ph) 170.64 (C-5, C-10).

EXAMPLE 13

N1,N6-di[(1S,2R)-2-hydroxy-2,3-dihydro-1H-1-indenyl]-(2R,3R,4R,5R)-2,5-di(4-fluorobenzyloxy)-3,4-dihydroxyhexanediamide A Preparation of 4-fluorobenzyl trichloroacetimidate.
Procedure as described in Example 7A but using 4-fluorobenzylalcohol gave (3.036 g, 81%).

$^1$H-NMR ($CDCL_3$, 250 MHz) δ 5.29 (s, 2H, H-4), 7.18–7.43 (m, 6H, Ph), 8.45 (s, 1H, NH) $^{13}$C-NMR ($CDCL_3$, 62.9 MHz) δ 70.02 (C-4), 91.35 (C-1), 115.32, 115.67, 129.77, 129.90, 131.26, (Ph), 162.40 (C-2).

B Preparation of 2,5-di-O-(4-fluorobenzyl)-L-mannaric-1,4:6,3-dilactone.
Procedure as described in Example 7B but using 4-fluorobenzyl trichloroaceimidate gave (0.242 g, 54%) as a white solid.

$^1$H-NMR (DMSO-$d_6$, 250 MHz) δ 4.74 (d, 4H, 2×Ph—$CH_2$, J=6.87), 4.87 (d, 2H, H-3, H-4, J=4.00), 5.24 (d, 2H, H-2, H-5, J=4.02), 7.18–7.47 (m, 8H, 2×Ph) $^{13}$C-NMR (DMSO-$d_6$, 62.9 MHz) δ 71.17 (C-3,C-4), 74.25 (C-2, C-5), 74.68 (2×Ph—$CH_2$), 114.92, 115.27, 130.00, 130.13, 133.07, (2×Ph), 171.54 (C-1, C-6).

C Prepared by the procedure as described in Example 10 but using 2,5-di-O-(4-fluorobenzyl)-L-mannaric-1,4:6,3-dilactone gave the title compound (0.053 g, 40%).

$^1$H-NMR (DMSO-$d_6$, 250 MHz) δ 2.78–3.11 (d+dd, 4H, H-1, H-14, J=4.63, 11.53, 16.08), 3.95 (t, 2H, H-3, H-12, J=7.64), 4.11 (d, 2H, H-7, H-8, J=8.04), 4,45 (m, 2H, H-6,

H-9), 4.51 (d, 4H, 2×Ph—CH$_2$; J=6.02), 4.89 (d 2H, 2×OH—CH, J=7.45), 5.10 (d, 2H, CH$_2$—OH, J=4.16), 527 (q, 2H, C-2, C-13, J=3.59, 4.96), 7.09–7.84 (m, 16H, 4×Ph), 8.30 (d, 2H, NH, J=8.74) $^{13}$C-NMR (DMSO-d$_6$, 62.9 MHz) δ 54.80 (C-1, C-14), 56.56 (C-3, C-12), 69.72 (2×Ph—CH$_2$), 70.38 (C-7, C-8), 72.02 (C-2, C-13), 79.36 (C-6, C-9), 114.68, 115.01, 124.23, 124.71, 126.09, 127.18, 129.62, 129.74, 134.15, 140.56, 141.92, 159.55, 163.40 (4×Ph), 170.81 (C-5, C-10).

EXAMPLE 14

N1,N6-di[(1S)-2-methyl-1-(methylcarbamoyl) propyl]-(2R,3R,4R,5R)-2,5-di[(4-phenylbenzyl) oxy]-3,4-dihydroxyhexanediamide A Preparation of 4-bromobenzyl trichioroacetimidate.

Procedure as described in Example 7A but using 4bromobenzylalcohol gave (3.2 g, 90%).

$^1$H-NMR (CDCL$_3$, 250 MHz) δ 5.3 (s, 2H), 7.3 (d), 7.5 (d), 8.4 (s). $^{13}$C-NMR (CDCL$_3$, 62.9 MHz) δ 69.84, 122.32, 129.40, 131.65, 134.38, 162.32.

B Preparation of 2,5-di-O-(4-bromobenzyl)-L-mannaric-1, 4:6,3-dilactone.

Procedure as described in Example 7B but using 4-bromobenzyl trichloroacetimidate gave (0.739 g, 83%).

$^1$H-NMR (DMSO-d$_6$, 250 MHz) δ 4.7 (d), 4.8 (d), 4.9 (d), 5.3 (d), 7.4 (d), 7.6 (d). $^{13}$C-NMR (DMSO-d$_6$, 62.9 MHz) δ 71.27, 74.40, 74.92, 130.08, 131.36, 136.44, 171.68.

C Preparation of N1,N6-di[(1S)-2-methyl-1-(methylcarbamoyl)propyl]-(2R,3R,4R,5R)-2,5-di[(4-bromobenzyl)oxy]-3,4-dihydroxyhexanediamide.

Procedure as described in Example 10 but using 2,5-di-O-(4-bromobenzyl)-L-mannaric-1,4:6,3-dilactone gave (0.0746 g, 66%).

$^{13}$C-NMR (DMSO-d$_6$, 62.9 MHz) δ 17.93, 19.81, 26.32, 30.84, 58.93, 72.11, 72.51, 80.72, 122.67, 130.36, 13229, 136.80, 172.35, 172.88.

D Preparation of the title compound. The product from above (30 mg, 0.039 mmol), phenylboracid (23.6 mg, 0.194 mmol), Pd(PPh$_3$)$_4$ (2.2 mg, 0.0019 mmol), NaCO$_3$ (77.6 µl, 2M), EtOH (60 µl), H$_2$O (80 µl) and dimethoxyethane (240 µl) was mixed in a reaction tube fitted with screw caps in an atmosphere of N$_2$. The tube was subjected to microwave irradiation for 4 min at 45 W. The tube was cooled in water before the reaction mixture was concentrated and purified by silica gel column chromatography (CHCl$_3$-MeOH 20: 1) to give 28 mg.

$^{13}$C-NMR (CDCl$_3$, 62.9 MHz) δ 17.08, 19.79, 26.18, 29.04, 58.42, 73.28, 73.64, 81.96, 127.20, 127.68, 128.96, 129.01, 135.26, 140.51, 141.71, 170.55, 172.53.

EXAMPLE 15

N1,N6-di[(1S)-2-methyl-1-(methycarbamoyl) propyl]-(2R,3R,4R,5R)-2,5-di[4-(3-thienyl) benzyloxy]-3,4-dihydroxyhexanediamide Preparation of the title compound. The product from Example 14C above (33 mg, 0.043 mmol), 3-thipheneboracid (23.9 mg, 0.214 mmol), Pd(PPh$_3$)$_4$ (2.5 mg, 0.00214 mmol), NaCO$_3$ (85 µl, 2M), EtOH (65 µl), H$_2$O (90 µl) and dimethoxyethane (270 µl) was mixed in a reaction tube fitted with screw caps in an atmosphere of N$_2$. The tube was subjected to microwave irradiation for 4 min at 45 W. The tube was cooled in water before the reaction mixture was concentrated and purified by silica gel column chromatography (CHCl$_3$-MeOH 20:1) to give 30 mg.

$^{13}$C-NMR (CDCl$_3$/MeOH-d$_4$ 62.9 MHz) δ 16.55, 18.42, 24.91, 29.54, 57.64, 70.96, 71.77, 79.38, 119.70, 125.34, 125.63, 125.76, 128.00, 135.14, 141.08, 171.32, 171.66. Anal.calcd. C, 61.61; H, 6.47; N, 7.19. Found: C, 61.2; H, 6.5; N 7.2.

EXAMPLE 16

N1,N6-di[(1S)-1-phenyl-1-(methycarbamoyl) methyl]-(2R,3R,4R,5R)-2,5-di(benzyloxy)-3,4-dihydroxyhexanediamide 2,5-di-O-benzyl-L-mamaric-1,4:6,3-di-lactone from Example 1 (150 mg, 0.423 mmol) was dissolved in acetonitrile (1 ml) and phenylglycine-N-methylamide (271 mg, 1.67 mmol) was added to the stirred solution. The solution was heated to 65° C. for 14 hours and then concentrated. The crude product was purified by silica gel column chromatography (chloroform-methanol 9: 1).

$^{13}$C-NMR (CD$_3$OD and CDCl$_3$) δ 26.3, 26.4, 57.1, 71.8, 73.4, 80.3, 127.4, 128.3, 128.4, 128.5, 128.6, 129.0, 136.5, 137.2, 170.3, 171.3. Anal.calcd. C, 66.85; H, 6.20; N, 8.21. Found: C, 66.74; H, 6.34; N 8.12.

EXAMPLE 17

N1,N6-di[(1S)-2-methyl-1-(methylcarbamoyl) propyl]-(2R,3R,4R,5R)-2,5-di[4-(3-fluorobenzyl) oxy]-3,4-dihydroxyhexanediamide A Tetrabutyl ammonium hydrogen sulphate (30 mg, 0.09 mmol) was added to 3-fluorobenzylalkohol (1.6 g, 124 mmol) in CH$_2$Cl$_2$ (15 ml) and KOH (50%, 15 ml). This mixture was cooled to −15° C. prior to the addition of tnichloroacetonitrile (1.5 ml, 14.9 mmol). After 30 min at −10° C. and 2.5 h at ambient temperature the phases were separated. The aqueous phase was extracted twice with CH$_2$Cl$_2$. The combined organic phases was dried with MgSO$_4$ and purified with silica gel column chromatography (toluene) to give 3-fluorobenzyl trichloroacetimidate (3.27 g, 95%) as a clear oil.

1H-NMR (CDCl$_3$) δ 5.3 (s), 7.0–7.15 (m), 7.3–7.45 (m), 8.4 (s).

B Preparation of 2,5-di-O-(3-fluorobenzyl)-L-mannaric-1, 4:6,3-dilactone.

Procedure as described in Example 7B but using 3-fluorobenzyl tnichloroacetimidate gave (0.220 g, 33%) as a white solid.

$^1$H-NMR (DMSO-d$_6$, 250 MHz) δ 4.8 (d, 4H, J=5.8), 4.9 (d, 2H, J=4.1), 5.25 (d, 2H, J=3.9), 7.15–7.25 (m, 8H), 7.3–7.35 (m, 2H). $^{13}$C-NMR (DMSO-d$_6$, 62.9 MHz) δ 71.08, 74.27, 74.67, 114.45, 114.80, 123.59, 130.30, 130.53, 139.8, 171.55.

C Prepared by the procedure as described in Example 7C, but using 2,5-di-O-(3-fluorobenzyl)-L-mannaric-1,4:6,3 dilactone gave the N1,N6-di[(1S)-2-methyl-1-(methylcarbamoyl)propyl]-(2R,3R,4R,5R)-2,5-di[4-(3-fluorobenzyl)oxy]-3,4-dihydroxybexanediamide (0.030 g, 16%) as a white solid.

EXAMPLE 18

N1,N6-di[(1S,2R)-2-hydroxy-2,3-dihydro-1H-1-indenyl]-(2R,3R,4R,5R)-2,5-di(3-fluorobenzyloxy)-3,4-dihydroxyhexanediamide Prepared by the procedure as described in Example 10 but usmg 2,5-di-O-(3-fluorobenzyl)-L-mannaric-1,4:6,3-dilactone from Example 17B (0.03 g, 0.08 mmol) and (1S,2R)-1-amino-2-indanol (0.046 g, 0.31 mmol) gave the title compound (0.04 g, 76%).

$^{13}$C-NMR (DMSO-$_6$, 62.9 MHz) δ 39.4, 56.6, 69.7, 70.2, 72.0, 79.5, 113.8, 113.9, 114.2, 114.3, 123.2, 124.2, 124.7, 126.1, 127.2, 130.0, 130.1, 140.6, 141.0, 141.1, 141.9, 160.1, 164.0, 170.7.

EXAMPLE 19

N1,N6-di[(1S)-2-methyl-1-methylcarbamoyl)propyl]-(2R,3R,4R,5R)-2,5-di[4-(2-fluorobenzyl)oxy]-3,4-dihroxyhexanediamide The procedure as described in Example 7C, but using 2,5di-O-(2-fluorobenzyl)-L-mannaric-1,4:6,3-dilactone (Example 12B) gave the title compound. (0.062 g, 38%) as a white solid.

$^{13}$C-NMR (DMSO-d$_6$, 62.9 MHz) 17.90, 19.11, 25.29, 30.43, 57.49, 64.78, 69.74, 79.38, 114.82, 115.15, 124.18, 124.59, 129.59, 130.14, 170.14, 170.93.

EXAMPLE 20

N1,N6-di[(1S)-2-methyl-1-(methylcarbamoyl)propyl]-(2R,3R,4R,5R)-2,5-di[4-(2,4-difluorobenzyl)oxy]-3,4-dihdrozyhexanediamide A Tetrabutyl ammonium hydrogen sulphate (15 mg) was added to 2,4-difluorobenzylalcohol (1.0 g, 6.94 mmol) in CH$_2$Cl$_2$ (10 ml) and KOH (50%, 10 ml). This mixture was cooled to −15° C. prior to the addition of trichloroacetonitrile (1.2 ml, 8.32 mmol). After 30 min at −15° C. and 3 h at ambient temperature the phases were separated. The aqueous phase was extracted twice with CH$_2$Cl$_2$. The combined organic phases were dried with MgSO$_4$ and reduced to one third. The residue was filtered through celite and concentrated to give the crude 2,4-difluorobenzyl trichloroacetimidate (1.83 g, 92%) as a yellow oil.

1H-NMR (CDCl$_3$) δ 5.35 (s), 6.75–6.90 (m), 7.50 (m), 8.50 (s). $^{13}$C-NMR (CDCl$_3$, 62.9 MHz) δ 64.1, 91.1, 103.9, 111.1, 118.6, 131.2, 158.9, 161.0, 162.3, 162.9, 165.2.

B Preparation of 2,5-di-O-(2,4-difluorobenzyl)-L-mannaric-1,4:6,3-dilactone. Procedure as described in Example 7B but using 2,4-difluorobenzyl trichloroacetimidate gave (0.97 g, 99%) the titled benzylated dilactone as a white solid.

$^1$H-NMR (DMSO-d$_6$, 250 MHz) δ 4.75 (t, 4H, J=2.1, 3.3), 5.20 (d, 4H, J=6.6), 6.9–7.1 (m, 4H), 7.5–7.65 (m, 2H).

C The benzylated dilactone from above (0.11 g, 0.28 mmol) and N-methyl-L-valine (0.22 g, 1.66 mmol) were refluxed in dichloromethane (1 ml) overnight. Concentration and purification by silica gel column chromatography (dichloromethane-methanol 9:2) gave the title diamide (0.042 g, 23%), as a white solid.

$^{13}$C-NMR (MeOH-d$_4$, 62.9 MHz) δ 18.4, 19.7, 26.2, 31.2, 59.9, 66.8, 72.1, 81.4, 104.2, 104.6, 104.9, 112.0, 112.4, 121.7, 122.1, 133.1, 133.2, 173.3, 173.8.

EXAMPLE 21

N1,N6-di[(1S,2R)-2-hydroxy-2,3-dihydro-1H-1-indenyl]-(2R,3R,4R,5R)-2,5-di(2,4-difluorobenzyioxy)-3,4-dihydroxyhexanediamide Procedure as described in Example 20C but using (1S, 2R)-1-amino-2-indanol (0.16 g, 1.09 mmol) gave the title compound (0.048 g, 25%), as a white solid.

$^1$H-NMR (MeOH-d$_4$, 62.9 MHz) δ 2.90 (2d, 2H), 3.15 (2d, 2H), 4.20 (d, 2H), 4.62 (m, 4H), 4.7 (s, 2H), 5.4 (d, 2H), 6.8–7.0 (m, 4H), 7.2–7.4 (m, 8H), 7.45–7.65 (m, 6H).

EXAMPLE 22

N1,N6-di[(1S)-2-methyl-1-(methylcarbamoyl)propyl]-(2R,3R,4R,5R)-2,5-di[4-(2-pyridyl)benzyloxy]-3,4-dihydroxyhexanediamide The product from Example 14C above (30 mg, 0.039 mmol), trimethyl-2-pyridyl tin (47.0 mg, 0.194 mmol), Pd(PPh$_3$)$_4$ (2.25 mg, 0.0010 mmol), DMF (1 ml) and CuO (3.1 mg, 0.039 mmol) were mixed in a reaction tube fitted with screw caps in an atmosphere of N$_2$. The tube was subjected to microwave irradiation for 2 min at 60 W. The mixture was diluted with CH$_2$Cl$_2$ (50 ml), washed with brine (3×20 ml), concentrated and purified by silica gel column chromatography (CH$_2$Cl$_2$-MeOH 15:1) to give 16 mg of the title compound.

$^{13}$C-NMR (CDCl$_3$/MeOH-d$_4$ 62.9 MHz) δ 18.6, 20.0, 26.4, 31.9, 60.1, 72.3, 73.2, 81.6, 122.7, 123.9, 128.3, 129.7, 139.1, 140.1, 150.4, 158.7, 173.7, 174.1.

EXAMPLE 23

N1,N6-di[(1S)-2-methyl-1-(methylcarbamoyl)propyl]-(2R,3R,4R,5R)-2,5-di[4-(2-pyridyl)benzyloxy]-3,4-dihydroxyhexanediamide The same procedure as for Example 22 above but using trimethyl-3-pyridyl tin (47.0 mg, 0.194 mmol) and purified by silica gel column chromatography (CHCl$_3$-MeOH 9:1) gave the title compound, 15 mg.

$^{13}$C-NMR (CDCl$_3$/MeOH-d$_4$ 62.9 MHz) δ 18.1, 20.0, 31.1, 59.2, 72.4, 73.0, 81.0, 125.1, 128.1, 129.7.

EXAMPLE 24

N1,N6-di[(1S)-2-methyl-1-(methylcarbamoyl)propyl]-(2R,3R,4R,5R)-2,5-di[(4-(3-nitrophenyl)benzyl)oxy]-3,4-dihydroxyhexanediamide The product from Example 14C above (200 mg, 0.259 mmol), 3-nitrophenylboracid (216.1 mg, 1.294 mmol), Pd(PPh$_3$)$_4$ (15.0 mg, 0.0129 mmol), NaCO$_3$ (259 μl, 2M), EtOH (773 μl), H$_2$O (1288 μl) and dimethoxyethane (3091 μl) were mixed in a reaction tube fitted with screw caps in an atmosphere of N$_2$. The tube was subjected to 80 ° C. overnight The mixture was diluted with CH$_2$Cl$_2$ (50 ml), washed with brine (3×20 ml), concentrated and purified by silica gel column chromatography(CHCl$_3$-MeOH 20:1) to give 206 mg of the title compound.

$^{13}$C-NMR (DMSO-d$_6$, 62.9 MHz) δ 18.1, 19.2, 25.4, 30.5, 57.6, 69.8, 70.7, 79.5, 120.9, 122.0, 126.8, 128.4, 130.4, 133.1, 137.0, 138.5, 141.4, 148.4, 170.0, 171.1.

EXAMPLE 25

N1,N6-di[(1S)-2-methyl-1-(methylcarbamoyl)propyl]-(2R,3R,4R,5R)-2,5-di[4-(2-thienyl)benzyloxy]-3,4-dihydroxyhexanediamide The product from Example 14C above (100 mg, 0.129 mmol), 2-thiophene boric acid (82.8 mg, 0.647 mmol), Pd(PPh$_3$)$_4$ (7.49 mg, 0.0065 mmol), NaCO$_3$ (129 μl, 2M), EtOH (386 μl), H$_2$O (644 μl) and dimethoxyethane (1546 μl) were mixed in a reaction tube fitted with screw caps in an atmosphere of N$_2$. The tube was subjected 80° C. overnight. The mixture was diluted with CHCl$_3$ (50 ml), washed with brine (3×20 ml), concentrated and purified by silica gel column chromatography(CHCl$_3$-MeOH 20:1) to give 88.8 mg of the title compound.

$^{13}$C-NMR (CDCl$_3$/MeOH-d$_4$ 62.9 MHz) δ 17.0, 18.3, 19.6, 26.0, 29.0, 50.7, 58.3, 72.9, 73.0, 81.4, 123.4, 125.2, 126.2, 128.1, 128.6, 131.9, 134.6, 135.3, 143.5, 170.7, 172.1. Anal. Found: C, 68.9; H, 6.33; N 7.36.

EXAMPLE 26

N1,N6-di[(1S,2R)-2-hydroxy-2,3-dihydro-1H-1-indenyl]-(2R,3R,5R)-2,5-di(benzyloxy)-3-hydroxyhexanediamide A To a stirred solution of the product from Example 10 above (400 mg, 620 mmol) in CH$_2$Cl$_2$ (3 ml) at 0° C. under an argon atmosphere was added lutidine (142 µl, 1.22 mmol) and t-butyldimethylsityl triflate (296 µl, 1.29 mmol). After 4 h, 1M NaOH (0.5 ml) was added and the mixture was washed with 1M HCl and brine. The organic layer was dried, concentrated and purified by silica gel column chromatography (CHCl$_3$-MeOH 80:1) to give the disilylated compound (313 mg, 355 µmol, 57%).

$^{13}$C NMR (CDCl$_3$) δ −4.8, 17.9, 25.7, 40.6, 56.3, 71.1, 74.0, 77.2, 124.5, 124.8, 126.9, 127.9, 128.2, 128.5, 136.7, 139.8, 140.9, 176.2.

B To a solution of the product from step a) above (922 mg, 1.05 mmol) in CH$_2$Cl$_2$ (21 ml) was added N,N-thiocaibonyldiimidazole (598 mg, 3.36 mmol). The mixture was refluxed for 22 h, concentrated and purified by silica gel column chromatography (toluene-EtOAc 3:1) to give (887 mg, 0.961 mmol, 92%) of the intermediate $^{13}$C NMR (CDCl$_3$) δ −4.8, −4.9, 17.8, 25.6, 40.5, 56.9, 74.3, 75.2, 78.2, 82.7, 124.6, 124.8, 126.6, 128.6, 128.8, 129.0, 135.6, 140.0, 141.5, 165.7, 192.0.

C To a refluxing solution of the product from step b) above in toluene (84 ml) under an argon atmosphere was added, a solution of tributyl tin hydride (0.70 ml, 2.6 mmol) and α,α'-azoisobutyronitrile (284 mg, 1.73 mmol) in toluene, over a period of 20 min. After 20 h additional tributyl tin hydride (0.23 ml) and α,α'-azoisobutyronitrile (71 mg) was added. After another 4 h the mixture was concentrated, dissolved in toluene and washed with 2.5 M NaOH and water, dried and concentrated. The residue was purified by silica gel column chromatography (toluene-EtOAc 3:1) to give (150 mg, 0.17 mmol, 20%).

$^{13}$C NMR (CDCl$_3$) δ −4.7, −4.8, 18.0, 25.7, 36.4, 40.5, 40.6, 56.3, 56.4, 69.8, 73.3, 74.0, 74.5, 82.0, 124.5, 124.7, 124.8, 126.9, 127.0, 127.1, 127.7, 127.9, 128.0, 128.2, 128.3, 128.4, 128.5, 136.7, 139.7, 141.2, 141.3, 171.3, 173.4.

D To a stirred solution of the product from step c) above (150 mg, 0.17 mmol) in MeOH (6 ml) was added H$^+$-Dowex. After 3 days at ambient temperature the mixture was filtered, concentrated and purified by silica gel column chromatography (CHCl$_3$-MeOH 20:1), followed by recrystallisation from MeOH, to give N1,N6-di[(1S,2R)-2-hydroxy-2,3-dihydro-1H-1-indenyl]-(2R,3R,5R)-2,5-di(benzyloxy)-3-hydroxyhexanediamide (38 mg, 0.060 mmol, 34%).

$^{13}$C NMR (CDCl$_3$-MeOH-d$_6$) δ 35.9, 39.8, 39.9, 57.2, 57.3, 69.2, 72.5, 72.7, 73.4, 74.0, 77.6, 84.0, 124.1, 124.2, 125.5, 127.2, 128.3, 128.4, 128.5, 128.8, 137.1, 140.2, 140.4, 140.6, 140.7, 171.4.

EXAMPLE 27
N1-[(1S,2R)-2-hydroxy-2,3-dihydro-1H-1-indenyl]-N6-(2-chloro-6-fluorobenzyl)-(2R,3R,4R,5R,)-2,5-di(2-fluorobenzmloxy)-3,4-dihydroxyhexanediamide A Preparation of (1S,2R)-1-phtalinido-2-indanol on solid support.

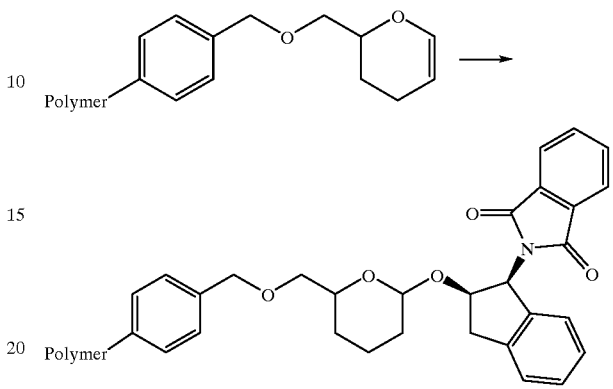

Dry Merrifield resin with a dihydropyran linker (300 mg, 2.1 mmol/g, 0.65 mmol linker) was swollen in 1,2-dichloroethane (4.2 ml) under an argon atmosphere. Anhydrous PPTS (300 mg, 1.2 mmol) and (1S,2R)-1-phtalimido-2-indanol (501 mg, 1.8 mmol) were added and the mixture was heated to 75° C. After 20 h the mixture was cooled to room temperature and the solid was rinsed with CH$_2$Cl$_2$ (20 ml), THF (10 ml) and dried under vacuum.

B Preparation of (1S,2R)-1l-amino-2-indanol on solid support.

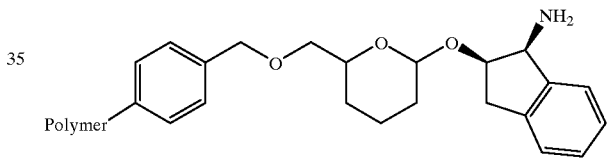

Methylamine in ethanol (4.0 ml, 33%) was added to the solid material from the previous step and stitred for 16 h. The resulting solid was rinsed with CH$_2$Cl$_2$ (10 ml), THF (10 ml), MeOH (10 ml) and CHCl$_3$ (10 ml) and dried under a vacuum.

C Preparation of N1-(2,5-di-O-(2-fluorobenzyl))-1,4-mannolactone-6-amide-N6-[(1S,2R)-2-hydroxy-2,3-dihydro-1H-1-indenyl] on solid support.

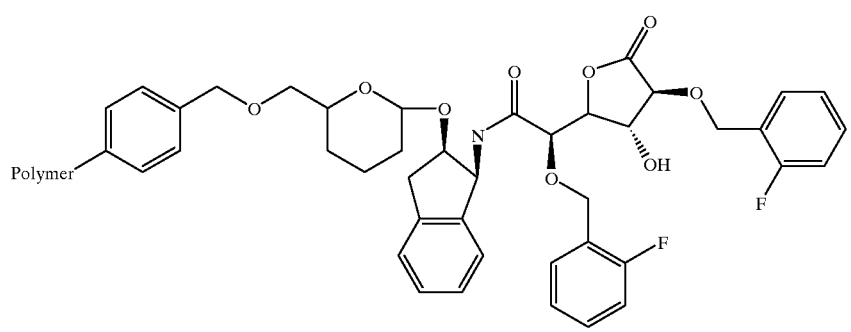

The solid material from the previous step was swollen in 1,2-dichloroethane (4.5 ml) for 40 minutes under an argon atmosphere. 2,5-Di-O-(2-fluorobenzyl)-L-mannaric-1,4:6,3-dilactone (Example 12B) (502 mg, 1.29 mmol) was added and the mixture was kept at 50° C. for 16 h before it was allowed to cool and rinsed with CH$_2$Cl$_2$ (10 ml) and CHCl$_3$ (10 ml).

D Preparation of N1-[(1S,2R)-2-hydroxy-2,3-dihydro-1H-1-indenyl]-N6-[2-chloro-6-fluorobenzyl]-(2R,3R,4R,5R,)-2,5-di(benzyloxy)-3,4-dibydroxyhexanediamide on solid support.

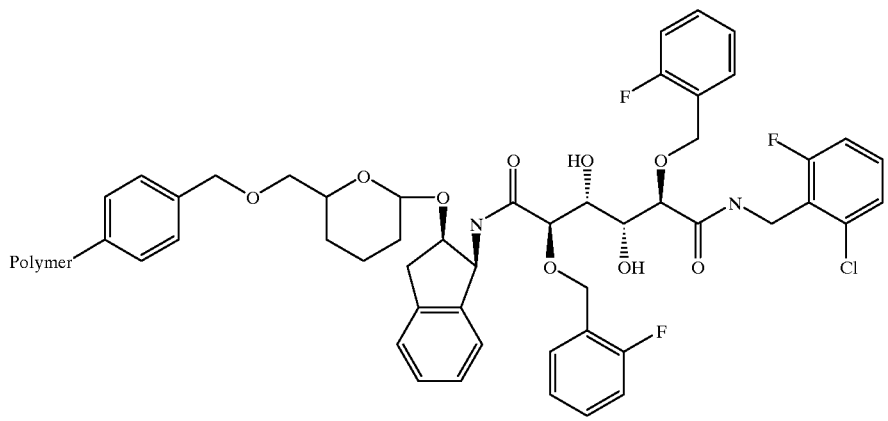

The solid material from the previous step was swollen in CH$_3$CN (4.5 ml) for 40 m under an argon atmosphere. 2-Chloro-6-fluorobenzylamine (249 mg, 1.56 mmol) was added and the mixture was kept at 50° C. for 16 h before it was cooled and rinsed with CH$_2$Cl$_2$ (10 ml) and CHCl$_3$ (10 ml).

E Preparation of N1-[(1S,2R)-2-hydroxy-2,3-dihydro-1H-1-indenyl]-N6-(2-chloro-6-fluorobenzyl)-(2R,3R,4R,5R,)-2,5-di(2-fluorobenzyloxy)-3,4-dihydroxyhexanediamide.

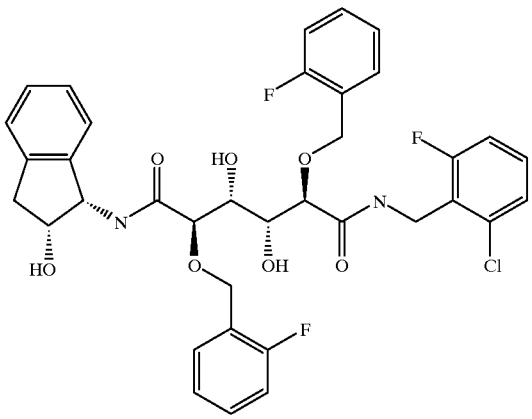

2.3 M HCl in methanol (8.5 ml) was added to the solid material from the previous step. After 4 h in an atmosphere of argon the solid was rinsed with CH$_2$Cl$_2$ (20 ml) and MeOH (20 ml). The combined organic layers were collected and combined and diluted with CHCl$_3$ (20 ml) and washed with sat. Aqueous NaHCO$_3$ (2×30 ml). The combined aqueous layers was extracted with CHCl$_3$ (2×40 ml). The combined organic layer was concentrated and purified with silica gel chromatography (CHCl$_3$-MeOH 40:1) to give the tide compound (68 mg, 23% yield based on the loading).

$^{13}$C NMR (CDCl$_3$) δ 34.3, 34.3, 39.2, 57.8, 67.4, 68.2, 71.3, 71.5, 72.4, 72.5, 79.8, 80.9, 114–140, 159.1, 159.2, 159.7, 162.8, 162.9, 163.4, 171.2, 172.1.

EXAMPLE 28

N1-[(1S,2R)-2-hydroxy-2,3-dihydro-1H-1-indenyl]-N6-[(1S)-2-methyl-1-([2-pyridylmethyl]carbamoyl)propyl]-(2R,3R,4R,5R)-2,5-di(benzyloxy)-3,4-dihydroxyhexanediamide A Preparation of N1-(2,5-di-O-benzyl)-1,4-mannolactone-6-amide-N6-[tertbutyl valine ester]. Tertbutyl valine ester (0.4 g) and the product from Example 1B in CH$_2$Cl$_2$ (50 ml) was kept at 4° C. for 16 h. Concentration and purification by silica gel column chromatography (EtOAc-hexane 1:2) gave (120 mg).

B Preparation of N1-[(1S,2R)-2-hydroxy-2,3-dihydro-1H-1-indenyl]-N6-[tertbutyl valin ester]-(2R,3R,4R,5R,)-2,5-di(benzyloxy)-3,4-dihydroxyhexanediamide. (1S,2R)-1-amino-2-indanol was added to a solution of the product from above in CH$_2$Cl$_2$ and left for 16 h. Concentration and silica gel column chromatography (EtOAc-hexane 1:2) gave (135 mg).

C Preparation of N1-[(1S,2R)-2-hydroxy-2,3-dihydro-1H-1-indenyl]-N6-[valine acid]-(2R,3R,4R,5R,)-2,5-di(benzyloxy)-3,4-dihydroxyhexanediamide. The product (120 mg) from above was subjected to TFA (5 ml) in 20 min. Concentration and drying in a vacuum gave (96 mg).

D Preparation of the tide compound. To the product from above in CH$_2$Cl$_2$ was added 1-hydroxybenzotriazole hydrate (14 μl), 2-aminomethylpyridine (20 mg) and 1,3-dicyclohexylcarbodiimide (35 mg). After 1h the mixture was directly purified by silica gel column chromatography (EtOAc-MeOH 9:1) gave (38 mg).

EXAMPLE 29

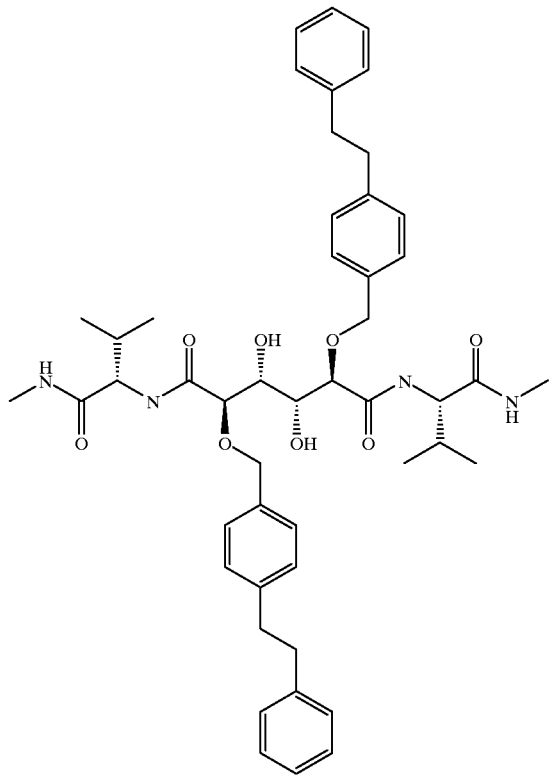

The P1 and P1' filling groups of the para-bromo analogue of the compound of Example 7 were extended as depicted above. Styrene (12.1 mg, 0.1165 mmol) and a little THF were added to a dessicated vessel under nitrogen on an ice bath. 9-BBN was added via injection under agitation. The mixture was allowed to come to room temperature and stirred for 4 hours. The brominated intermediate, prepared analogously to example 7, (30 mg, 0.002 mmol), K$_2$CO$_3$ (21.45 mg, 0.155 mmol) and Pd(PPh$_3$) (2.70, 0.002 mmol) in 1 ml DMF were added under nitrogen and heated overnight at 50° C. Around 50 ml chloroform is added and the mixture shaken with 3×30 ml brine, dried and evaporated under vacuum overnight. The above depicted product is purified by silica gel chromatography.

$^{13}$C NMR (CDCl$_3$) δ 172.5, 170.2, 142.4, 141.4, 133.6, 128.9, 128.3, 128.1, 126.0, 82.0, 73.6, 73.3, 58.3, 37.5, 28.7, 25.9, 19.7, 16.8.

EXAMPLE 30

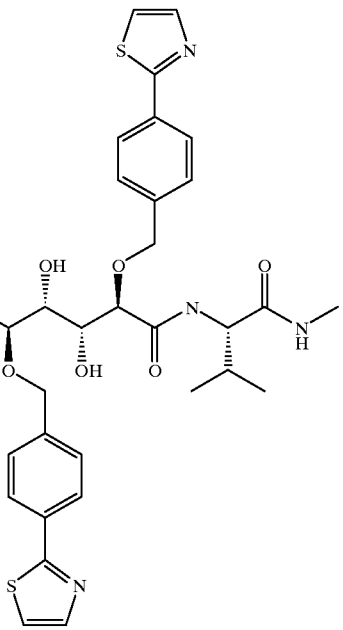

Tributyl-2-thiazolyl tin (72.6 mg, 0.19 mmol), Pd(PPh$_3$)$_4$ (2.25 mg, 0.002 mmol), the brominated analogue of Example 7 (30 mg, 0.034 mmol) Ag$_2$O (9.0 mg, 0.04 mmol) in 1ml DMF were added to a microtube and microwaved for 2 minutes at 60 W. 50 ml chloroform was added and the mixture washed with 3×20 ml brine. The organic phase was dried and evaporated ot yield the tide compound.

$^{13}$C NMR (CDCl$_3$) δ 173.3, 172.7, 144.0, 140.4, 133.8, 129.4, 127.5, 120.4, 81.2, 72.8, 72.2, 59.3, 31.1, 26.5, 19.9, 18.1.

EXAMPLE 31

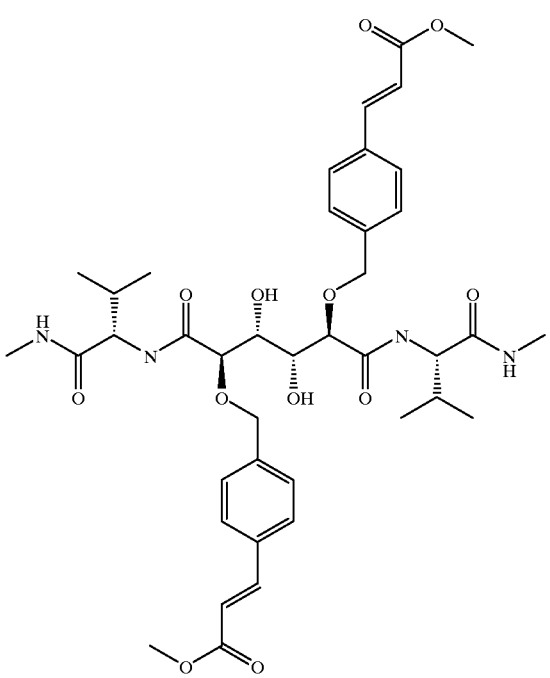

A mixture of the brominated analogue of Example 7, (38.6 mg, 0.05 mmol), methyl acrylate (21.5 mg, 0.25 mmol), diisopropyl ethylaniine (25.8 mg, 0.2 mmol), Pd(OAc)$_2$ (1.12 mg, 0.05 mmol), (o-tol)$_3$P (3.65 mg, 0.012 mmol) and water (0.15 ml) in DMF (0.85 ml) was degassed under a nitrogen flow for 10 minutes. The reaction mixture was stirred and heated to 100° C. for 48 hours. The reaction mixture was allowed to cool and poured into saturated accqueous sodium chloride solution (10 ml). The aqueous layer was extracted with dichloromethane (3×10 ml) and the combined organic phases were washed with saturated aqueous sodium chloride solution (3×5 ml), dried over MgSO$_4$, filtered and concentrated at reduced pressure. The residue was purified on a silica gel colunm to give the above depicted product (27 mg, 69%).

$^{13}$C NMR (CDCl$_3$) δ 171.7, 171.6, 171.5, 167.7, 144, 139.2, 134.3, 131.7, 129.6, 128.4, 118.0, 80.5, 77.7, 77.2, 76.7, 72.4, 71.8, 51.8, 49.7, 49.4, 49.1, 48.8, 48.5, 29.8, 25.9, 19.4, 17.3.

EXAMPLE 32

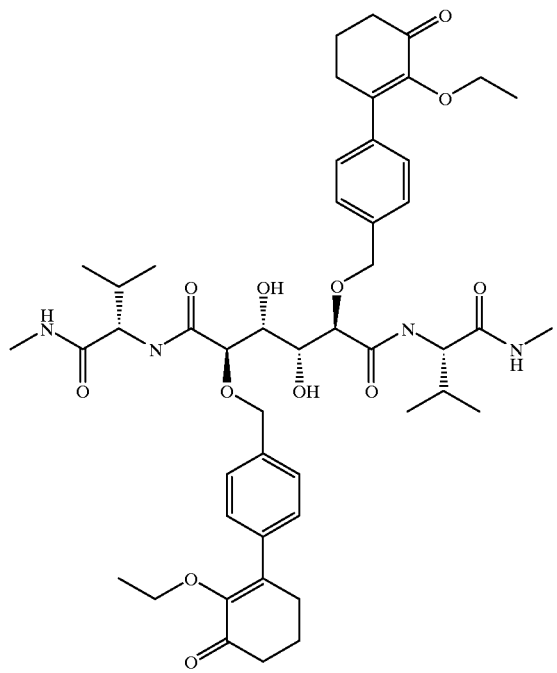

Repeating the reaction conditions of example 31 with 2-ethoxy-3-keto-1-cyclohexadiene, gave a mixture of compounds which separated by 7% MeOH in dichloromethane (preparative plate) to yield 66 mg of the crude product depicted above.

$^{13}$C NMR (CDCl$_3$) δ 171.5, 137.3, 137.0, 128.5, 128.2, 128.0, 127.4, 80.5, 77.5, 77.2, 77.0, 765, 72.4, 71.8, 67.9, 58.0, 50.0, 49.7, 49.3, 49.0, 48.7, 48.4, 48.1, 38.7, 30.6, 29.5, 25.6, 22.3, 19.3, 17.1, 15.1

EXAMPLE 33

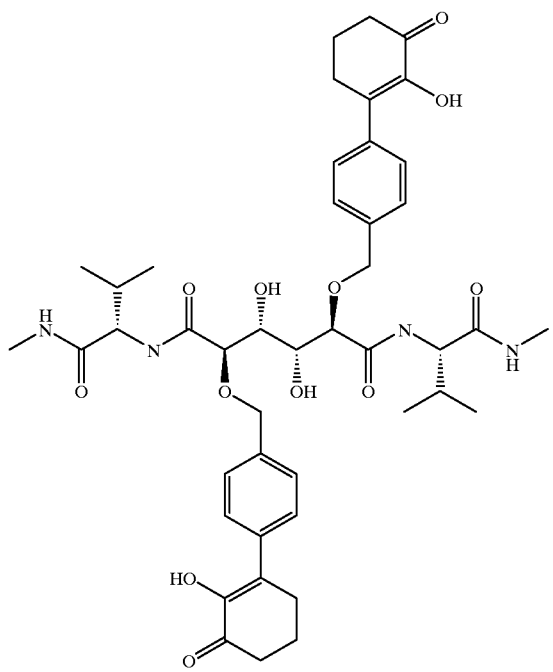

To a solution the compound of example 32 (18 mg, 0.02 mmol) in CH$_2$Cl$_2$ was added 1-N-boron tribromide (0.1 ml) dropwise over 5 minutes at $-_{78}$° . The reaction mixture was stirred at this temperature for 30 min and the n kept in a refrigerator for 2 hours at −12° C. the reaction mixture was poured into saL aqueous NaCl solution (5 ml), extracted with dichloromethane (3×5 ml) and the combine organic layers washed with sat aqueous NaCl solution (2×5 ml), dried over MgSO$_4$, filtered and concentrated at reduced pressure. The residue was purified on a silica gel column to give a crude preparation of the above depicted structure, (9.8 mg, 58%).

$^{13}$C NMR (CDCl$_3$) δ 171.5, 136.5, 128.4, 127.9, 127.6, 80.3, 77.5, 76.5, 72.4, 71.8, 58.0, 49.9, 49.6, 49.3, 48.6, 48.3, 48.0, 35.7, 29.5, 28.6, 25.7, 22.4, 19.3, 17.1

Biological Example 1

Representative compounds were tested for HIV protease activity in a spectrophotometric enzyme assay using the chromogenic substrate His-Lys-Ala-Arg-Val-Leu-p-nitro-Phe-Glu-Ala-Nle-Ser-amide and purified HIV proteinase. The rate of cleavage is followed by continuously registering the change in absorbance at 300 nm. The IC$_{50}$ representing the compound concentration which inhibits enzyme perfoimance by 50% is calculated from the dose response curve. However, the compounds of the invention are so extremely active that affinity constants (K$_i$) are idicated to provide a more effective comparison between compounds.

Compounds are also tested for HIV protease activity in cell culture. MT4 cells grown in RPMI 1640 cell culture medium including 10% fetal calf serum are infected with 10 1TCID HIV-1 per 2×10$^5$ cells and cultured for 6 days. XTT is added and the amount of XTT formazan produced in the following 6 hours represents the number of surviving cells. Results are expressed as the ED$_{50}$, that is the concentration in μg/ml of the compound of the invention which suppresses viral replication by 50%.

Antiviral activities for representative compounds of the invention are shown in Table 1.

TABLE 1

|  | IC$_{50}$ μM (K$_i$ μM) | ED$_{50}$ μg/ml |
|---|---|---|
| Example 1 | 0.015 | 0.5 |
| Example 3 | 0.004 | 0.5 |
| Example 4 | (0.009) | 1 |
| Example 7 | (0.0023) | 5 |
| Example 8 | (0.0034) | 6 |
| Example 9 | (0.0035) | 0.4 |
| Example 10 | (0.0016) | 0.05 |
| Example 11 | 0.0012 | 0.2 |
| Example 12 | (0.00013) | 0.04 |
| Example 13 | (0.00007) | 0.2 |
| Example 14 | (0.00067) | 0.04 |
| Example 15 | (0.0012) | 0.03 |
| Example 16 | (0.0023) | 1 |
| Example 17 | (0.002) | 0.8 |
| Example 18 | (0.050) | 0.5 |
| Example 19 | (0.0005) | 0.8 |
| Example 20 | (0.0001) | 0.9 |
| Example 21 | (0.00038) | 0.1 |
| Example 22 | (0.00061) | 0.4 |
| Example 23 | (0.0019) | 2 |
| Example 24 | (0.0014) | 0.4 |
| Example 25 | (0.00017) | 0.02 |
| Example 26 | (0.00097) | 0.8 |
| Example 27 | (0.0014) | 0.8 |
| Example 28 | ND | 0.2 |
| Example 31 | (0.00009) | 0.3 |
| Example 32 | (0.0003) | 0.2 |
| Example 33 | (0.0005) | 0.2 |

What is claimed is:

1. A compound of the formula IV

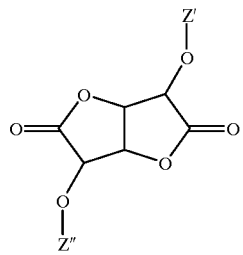

where Z' and Z" are —(CH$_2$)$_m$P wherein each m is independently 0, 1 or 2 and each P is independently a substituted or unsubstituted member selected from the group consisting of phenyl, cyclohexenyl, cyclopentyl, cyclohexanyl, cyclopentanyl, indanyl, naphthyl, furyl, thienyl, pyrrolyl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl and bicyclic rings.

2. A compound as defined in claim 1, having the stereochemistry:

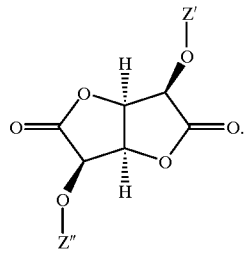

3. A compound according to claim 1, wherein Z' and Z" are each independently benzyl, 2-fluorobenzyl, 2-methylbenzyl, 2,4-difluorobenzyl, 4-fluorobenzyl, 4-bromobenzyl, 4-phenylbenzyl, 4-thiophenylbenzyl, 4-(4'-nitrophenyl)benzyl, 4-thienylbenzyl, 4-thiazolylbenzyl or 4-(pyridyl)benzyl.

4. A compound according to claim 1 wherein both Z' and Z" are identical.

5. The compound according to claim 1, wherein the carbo- or heterocyclic moiety of Z' and Z" each independently contains one to three substituents selected from the group consisting of halo, amino, mercapto, oxo, nitro, NHC$_1$–C$_6$ alkyl, N (C$_1$–C$_6$ alkyl)$_2$, C$_1$–C$_6$ alkyl, C$_1$–C$_6$ alkenyl, C$_1$–C$_6$ alkynyl, C$_1$–C$_6$ alkanoyl, C$_1$–C$_6$ alkoxy, thioC$_1$–C$_6$ alkyl, thioC$_1$–C$_6$ alkoxy, hydroxy, hydroxyC$_1$–C$_6$ alkyl, haloC$_1$–C$_6$ alkyl, aminoC$_1$–C$_6$ alkyl, C$_1$–C$_6$ alkyl, cyano, carboxyl, carbalkoxy, carboxamide, carbamoyl, sulfonylamide, benzyloxy, morpholyl-C$_1$–C$_6$ alkyloxy, phenyl, cyclohexenyl, cyclopentyl, cyclohexanyl, cyclopentanyl, indanyl, napthyl, furyl, thienyl, pyranyl, pyrrolyl, pyrrolinyl, pyrrolidinyl, pyrazolyl, pyrazolinyl, pyrazolidinyl, imidazoyl, imidazolinyl, imidazolidinyl, pyridyl, piperidiniyl, pyrazinyl, piperazinyl, pyrimidinyl, pyridazinyl, oxazoly, oxazolidinyl, isoxazolyl, isoxazolidinyl, morpholinyl, thiazolyl, thiazolidinyl, isothiazolyl, isothiazolidinyl, bicyclic rings of the above fused to a phenyl ring.

6. The compound according to claim 5, wherein said substituent is spaced by an alkyl.

7. The compound according to claim 6, wherein said substituent is a C1-3 alkylaryl.

8. The compound according to claim 1, wherein Z' and Z" are each independently substituted or unsubstituted benzyl.

9. The compound according to claim 8, wherein each said benzyl independently contains 1, 2 or 3 substituents selected from the group consisting of fluoro, chloro, hydroxy, amino, —NH(C$_{1-6}$ alkyl), —N(C$_{1-6}$ alkyl)$_2$, —NPh(C$_{1-6}$ alkyl), —NHPh, methoxy, cyano, hydroxymethyl, aminomethyl, alkysulfonyl, carbamoyl morpholinethoxy, benzyloxy, and benzylamide.

10. The compound according to claim 6, wherein said benzyl contains 1 or 2 fluoro substituents.

11. The compound according to claim 3, wherein Z' and Z" are each independently 2-fluorobenzyl or 2,4-fluorobenzyl.

12. The compound according to claim 1, wherein said bicyclic ring is comprised of a phenyl ring fused to a substituted or unsubstituted member selected from the group consisting of phenyl, cyclohexenyl, cyclopentanyl, indanyl, napthyl, furyl, thienyl, pyrrolyl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, and isothiazolidinyl.

13. The compound according to claim 12, wherein said bicyclic ring is indolyl, quinolinyl, isoquinolinyl, benzimidazolyl, benzothiazolyl, benzoxazolyl or benzothienyl.

* * * * *